US005530764A

United States Patent [19]

Uchida et al.

[11] Patent Number: 5,530,764

[45] Date of Patent: Jun. 25, 1996

[54] VIBRATION CONTROL SYSTEM FOR AN AUTOMOTIVE VEHICLE

[75] Inventors: Hiroshi Uchida; Tetsuro Butsuen; Norihiko Nakao, all of Hiroshima-ken, Japan

[73] Assignee: Mazda Motor Corporation, Hiroshima-ken, Japan

[21] Appl. No.: 214,631

[22] Filed: Mar. 18, 1994

[30] Foreign Application Priority Data

Mar. 19, 1993 [JP] Japan .................................... 5-085305
Mar. 26, 1993 [JP] Japan .................................... 5-092255

[51] Int. Cl.$^{6}$ ............................ H03B 29/00; A61F 11/06

[52] U.S. Cl. ................................................ 381/71; 381/94

[58] Field of Search .............................. 381/71, 94, 73.1, 381/86

[56] References Cited

U.S. PATENT DOCUMENTS

| | | | |
|---|---|---|---|
| 5,293,578 | 3/1994 | Nagami et al. | 381/71 |
| 5,319,715 | 6/1994 | Nagami et al. | 381/71 |
| 5,321,759 | 6/1994 | Yuan | 381/71 |
| 5,337,365 | 8/1994 | Hamabe et al. | 381/94 |

FOREIGN PATENT DOCUMENTS 1501344 3/1989 Japan .

*Primary Examiner*—Forester W. Isen
*Assistant Examiner*—Xu Mei
*Attorney, Agent, or Firm*—Sixbey, Friedman, Leedom & Ferguson; Gerald J. Ferguson, Jr.; Donald R. Studebaker

[57] ABSTRACT

Periodic first vibrations generated from the engine are reduced by the interference with the second vibrations generated from the speakers disposed in the vehicle compartment of the vehicle. The second vibrations are set in a cycle unit of the first vibrations, and they are corrected (optimized) on the basis of the signals from the microphones detecting the vibrations within the vehicle compartment and the transmission characteristic between the microphones and the speakers. During a transient period of time during which the cycles vary (during which the data lengths of the data of the second vibrations vary), such as by acceleration or deceleration, the data on the vibration wave form of the previous vibrations is corrected in anticipation (i.e. the data length is corrected), the current vibration wave form is set. The correction of the data length is made by inserting a given number of estimated data values into the previous data length or by deleting a given number of the data values from the previous data length. Further, the data length can be corrected by extending or contracting the previous vibration wave form as a whole so as to provide the data length in accordance with the current vibration wave form.

17 Claims, 23 Drawing Sheets

$\Delta t_1$ = PREVIOUS $\Delta t_n$ + PREVIOUS $\tau$ $$\Delta t_2 = \Delta t_1 + \tau$$

$$\Delta t_3 = \Delta t_2 + \tau$$

$$\vdots$$

$$\Delta t_n = \Delta t_{n-1} + \tau$$

$$\tau = \frac{2(\text{CURRENT OUTPUT WAVE CYCLE} - \text{FOLLOWING OUTPUT WAVE CYCLE})}{n(n-1)}$$

$$n = \frac{\text{FOLLOWING OUTPUT WAVE CYCLE}}{\Delta t}$$

VIBRATION CONTROL SYSTEM FOR AN AUTOMOTIVE VEHICLE

BACKGROUND OF THE INVENTION

1. Field of the Invention

The present invention relates to a vibration control system for an automotive vehicle for controlling vibrations, i.e. noise, of the vehicle and, more particularly, to a vibrations control system for an automotive vehicle for controlling the vibrations of the vehicle, so adapted as to reduce the vibrations by the interference with vibrations generated from another source of vibrations.

2. Description of the Related Art

Vibration of an automotive vehicle, particularly noise of the internal combustion engine of the vehicle, i.e. first vibrations, may disturb the driver and the passengers. It is thus proposed that the first vibrations be reduced by creating vibrations for reducing the first vibrations, i.e. second vibrations, from a speaker or the like and by causing the second vibrations to interfere with the first vibrations.

For example, Japanese Patent Unexamined Publication Kokai No. 1-501,344 discloses a vibration control system of this kind, which comprises a reference signals generating unit for picking up a signal corresponding to the vibrations of a vibration source, i.e. to first vibrations, as a reference signal; a microphone for picking up the vibrations in a predetermined space of the vehicle body, in which the noise by the first vibrations causes problems; a speaker for generating second vibrations toward or inside the predetermined space thereof; an adaptive-type digital filter for creating the second vibrations to be generated from the speaker; and an algorithm operating unit for sequentially optimizing a filter coefficient of the filter. This control system can create the second vibrations by allowing the adaptive-type digital filter to adjust the gain or phase of the reference signal in accordance with the reference signal, and the filter coefficient of the adaptive-type digital filter is sequentially optimized by the algorithm operating unit so as to reduce the first vibrations detected by the microphone. Further, the least square is generally employed as the algorithm for optimization.

The vibrations control system disclosed in the above-mentioned prior patent publication has the advantage that various vibrations can be reduced, but it presents the drawbacks that the amount of computations becomes so voluminous that it is difficult to ensure a sufficient extent of responsiveness and that an arithmetic unit of high quality is required. In particular, the volume of computation becomes extremely large when the number of speakers and microphones becomes large.

From the above-mentioned point of view and in order to solve the problems inherent in the prior art control system, the present inventors have previously developed a vibrations control system for reducing the first vibrations with the fact taken into consideration that the vibrations of the engine for the automotive vehicle to be deadened, i.e. the first vibrations, are generally periodic. This vibrations control system can create the vibrations for reducing the first vibrations to an extremely great extent and it does not require an arithmetic unit of high quality.

This vibrations control system of this prior art comprises a cycle detecting means for detecting a cycle of first vibrations caused by a first vibrations source such as an engine, a second vibrations source, such as a speaker, for generating second vibrations for reducing a vibration energy of the first vibrations, a vibration detecting means, such as a microphone, for detecting the vibrations in a position of, for example, a vehicle compartment, in which the vibrations are desired to be reduced, a vibration energy setting means for setting a vibration energy of the second vibrations generated by the second vibrations source at each cycle detected by the cycle detecting means, and a correction means for correcting an output from the vibration energy setting means on the basis of an output of the vibration detecting means and a transmission characteristic between the vibration detecting means and the second vibration source.

This arrangement of the prior art vibration control system can present the advantages that it can collectively implement the processing of creating a wave form of the second vibrations and the processing of vibrations picked up by the vibration detecting means, such as the microphone, for every one cycle on the basis of the cycle detected by the cycle detecting means, thereby extremely simplifying the computation for optimizing the wave form of the second vibrations.

Further, this arrangement of the prior art vibrations control system for reducing the periodic vibrations as described hereinabove can sufficiently reduce the vibrations when the cycles of the first vibrations are constant, i.e. when the vehicle is running at a constant speed, although this prior art vibrations control system cannot compete with single-occurring vibrations or unforeseen vibrations. When the cycles of the first vibrations are varying, for example, during the time when the vehicle is being accelerated or decelerated, the prior art system suffers from the disadvantage that the vibrations cannot be reduced to a sufficient extent.

As the second vibrations for reducing the first vibrations can be set primarily by digital control, data values in the number corresponding to one cycle portion of the first vibrations are created in the form in which they exist in every sampling cycle, i.e. in the form of vector, and the data values set in each sampling cycle are created as amplitude, i.e. as a vibration energy, in each phase of the second vibrations. If the number of data becomes large, a wave form for one cycle portion becomes long resulting in a long data length. Hence, the data of the second vibrations to be generated at this time, i.e. the current data of the second vibrations, is optimized by utilizing the data of the second vibrations previously generated, i.e. the previous data of the second vibrations. If the cycle would vary, however, the numbers of the current data and the previous data, i.e. their data lengths corresponding to one cycle portion, also vary and the second vibrations cannot be optimized at its portion corresponding to the difference in the data length, resulting in a failure to reduce the first vibrations to a sufficient extent. For example, if the data length of the current data is lengthened and its data number is increased to 12 from the previous data number of 10, the number of data lacks by two for creating the data length of the current data. On the contrary, the number of data becomes in excess if the data length would be shortened.

On the other hand, even if current second vibrations would be generated in the data length of the second vibrations previously generated, the first vibrations can be reduced to a considerably great extent. Further, when the running status of the vehicle would be returned to its ordinary running status after acceleration or deceleration, the optimization proceeds and the first vibrations can be reduced to a sufficient level. However, as the first vibrations cannot be reduced sufficiently during a period of time during which the cycles of the data varies, the first vibrations cannot be said to be reduced to a satisfactory level as a whole.

SUMMARY OF THE INVENTION

Therefore, the present invention has the object to provide a vibration control system for an automotive vehicle so adapted as to reduce the vibrations of the vehicle body even during a transient period of time during which the cycles of the vibrations to be reduced vary, given the correction, i.e. optimization, of the vibrations for reducing the first vibrations in every cycle of the periodic vibrations to be reduced.

In order to achieve the aforesaid object, the present invention has the object to provide a vibration control system for an automotive vehicle so adapted as to reduce periodic vibrations created and generated by a first vibration source in a predetermined space of the vehicle compartment of the vehicle, which comprises:

a cycle detecting means for detecting a cycle of first vibrations;

a second vibration source for generating second vibrations for reducing a vibration energy of the first vibrations;

a vibration detecting means for detecting vibrations in the predetermined space of the vehicle compartment;

a vibration energy setting means for setting a vibration energy of the second vibrations generated from the second vibration source at every one cycle detected by the cycle detecting means;

a correction means for correcting an output from the vibration energy setting means on the basis of an output from the vibration detecting means as well as a transmission characteristic between the vibration detecting means and the second vibration source; and a data length correcting means for correcting a data length of data of the previously generated second vibrations in anticipation and providing an expected data of the currently generating second vibrations having the number of data corresponding to the data length of data of the currently generating second vibrations, when the data length of the data of the currently generating second vibrations to be set in correspondence with the current cycle differs from the data length of the data of the previously generated second vibrations set in correspondence with the previous cycle of the previously generated second vibrations.

This arrangement of the vibrations control system according to the present invention can reduce the vibrations to a sufficient level by subjecting the data length of the data of the second vibrations to optimization in anticipation even during a transient period of time during which the cycles of the first vibrations vary. In other words, the vibrations can be reduced sufficiently by optimizing the wave form of the vibrations to be defined by the current data length of the current data to be currently generated, without greatly changing the wave form of the vibrations defined by the previous data length of the previously generated data as a whole, even during such a transient period of time.

The data length correcting means may be arranged in a manner as will be described hereinafter. Specifically, the data length correcting means is adapted to insert an estimated data value into the previous data length of the previous data or to delete a data length from the previous data length thereof so as to make the number of data comply with the current data length of the current data.

Additionally, the data length correcting means may specifically be structured in a manner as capable of correcting the data length by contracting or extending the wave form of the second vibrations previously generated as a whole so as to make the number of data comply with the current data length of the current data.

In particular, this arrangement of the data length correcting means can sufficiently reduce the vibrations even during the transient period of time because the wave form of the second vibrations can be provided in correspondence with the data length of the currently generating second vibrations, while the data value of the second vibrations can be maintained in a substantially optimal state at each phase of the wave form by shortening or extending the wave form of the previously generated second vibrations in anticipation so as to comply with the data length of the data of the second vibrations to be generated currently.

Other objects, features and advantages of this invention will become apparent in the course of the description of the preferred embodiments, which follows, with reference to the accompanying drawings.

DESCRIPTION OF THE PREFERRED EMBODIMENTS

The present invention will be described more in detail with reference to the accompanying drawings.

Outline

Figure 1:
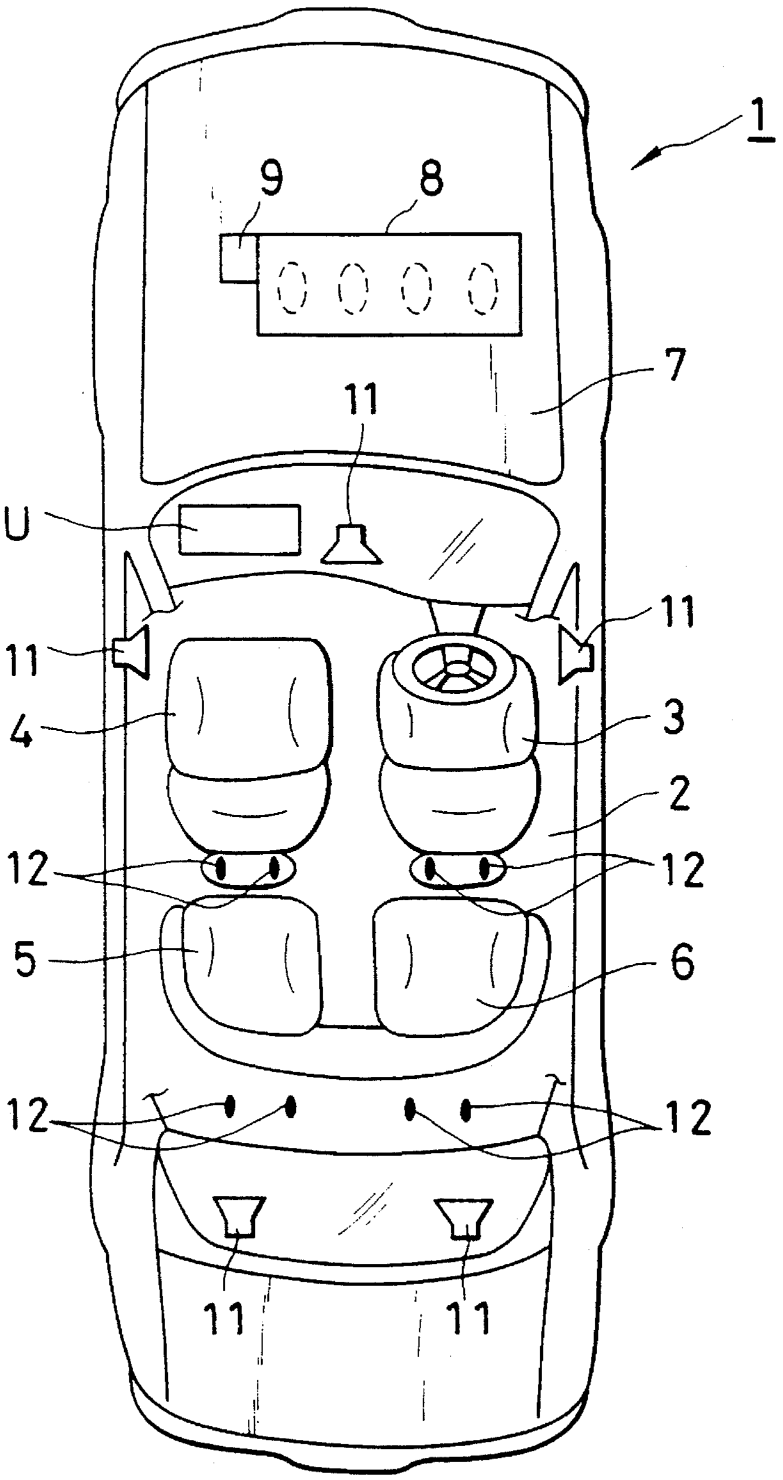
FIG. 1 is a schematic representation showing an outline of the body of a vehicle, with its roof excluded, to which the vibrations control system according to this invention is applied, when looked from the upside.

FIG. 1 shows the body 1 of an automotive vehicle which has a vehicle compartment 2 provided with a driver's seat 3 and an assistant driver's seat 4 and rear seats 5 and 6. An engine room 7 is mounted with a in-line 4-cylinder engine 8 having an ignition coil 9.

In the embodiment of this invention, the engine 8 is a source generating noises that generate periodic vibrations in accordance with the number of revolutions of the engine, that is, a first vibration source. The vehicle compartment 2 is a predetermined space in which the noises of the engine 8, i.e. the first vibrations, should be reduced, and is provided with five speakers, referred collectively to as reference numeral 11, and with eight microphones, referred collectively to as reference numeral 12. Each of the speakers 11 functions as a second vibration source for generating second vibrations for reducing the noises of the engine 8 in the vehicle compartment 8, and each of the microphones 12 functions as a vibration detecting means for detecting the actual vibrations in the vehicle compartment 8.

Figure 2:
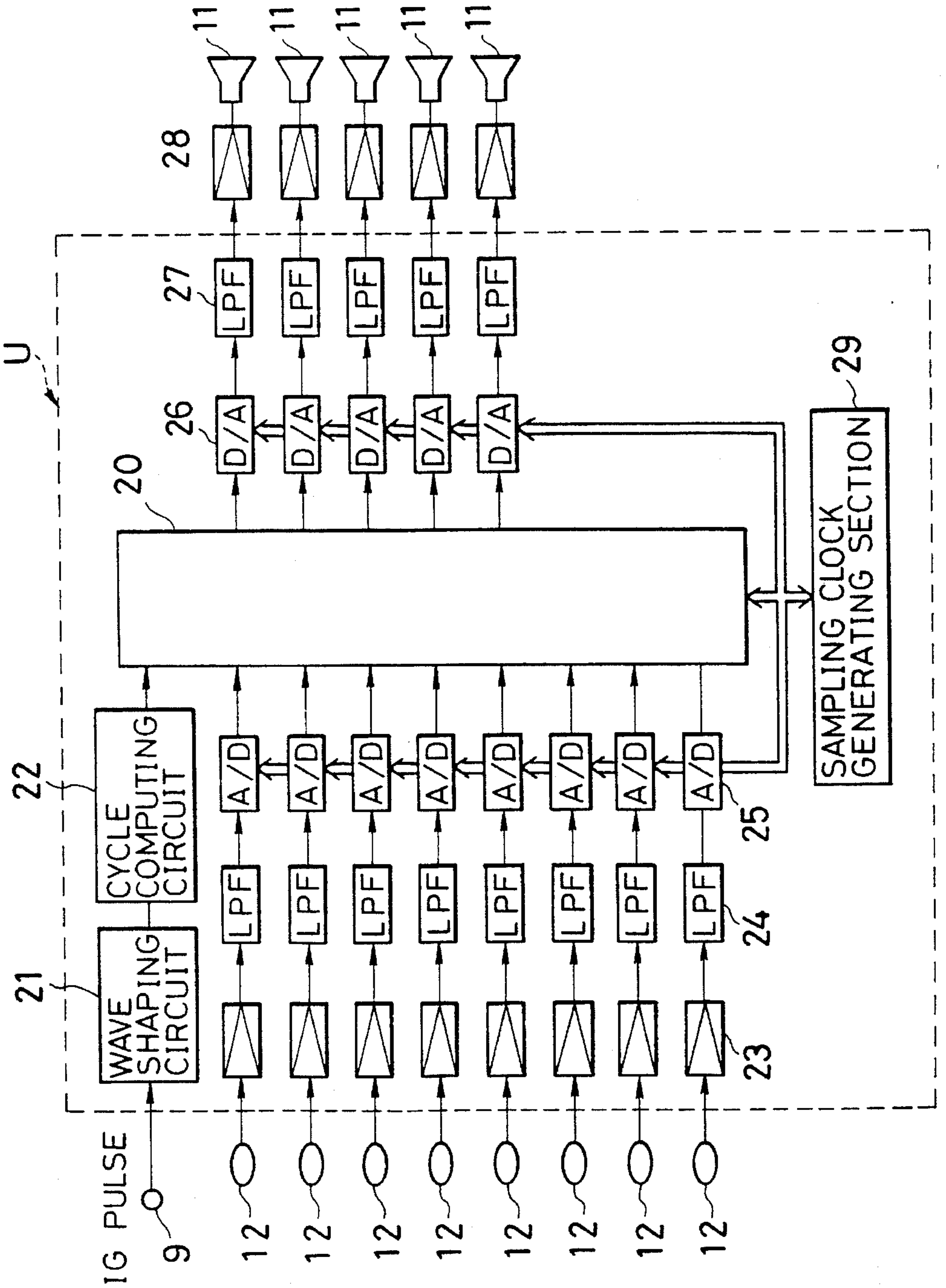
FIG. 2 is a block diagram showing an example of an outline of a control system for the vibrations control system according to an embodiment of this invention.

The vehicle 1 has a control unit U composed of a microcomputer with a control section 20 consisting of a CPU. As shown in FIG. 2, the control section 20 is supplied with signals from a primary coil of the ignition coil 9, i.e. ignition pulse signals in accordance with the number of engine revolutions, through a wave form shaping circuit 21 and a cycle computing circuit 22, and with signals from each of the microphones 12 through an amplifier 23, a low-pass filer 24 and an A/D converter 25. On the other hand, the control section 20 generates signals to each of the speakers 11 through a D/A converter 26, a low-pass filter 27, and an amplifier 28.

The control section 20 can optimize the second vibrations to be generated from each of the speakers 11 so as to reduce the first vibrations to be detected by the microphones 12.

Then, a description will be made of the basic mode of creation of the second vibrations and of the correction of the second vibrations during the transient period of time during which their cycles vary.

Basic Mode of Creation of Second Vibrations

First, a description will be made of the basic mode of creation of the second vibrations, i.e. the mode of the creation of the second vibrations with the presumption that the cycles in accordance with the IG pulses are constant.

Figure 3:
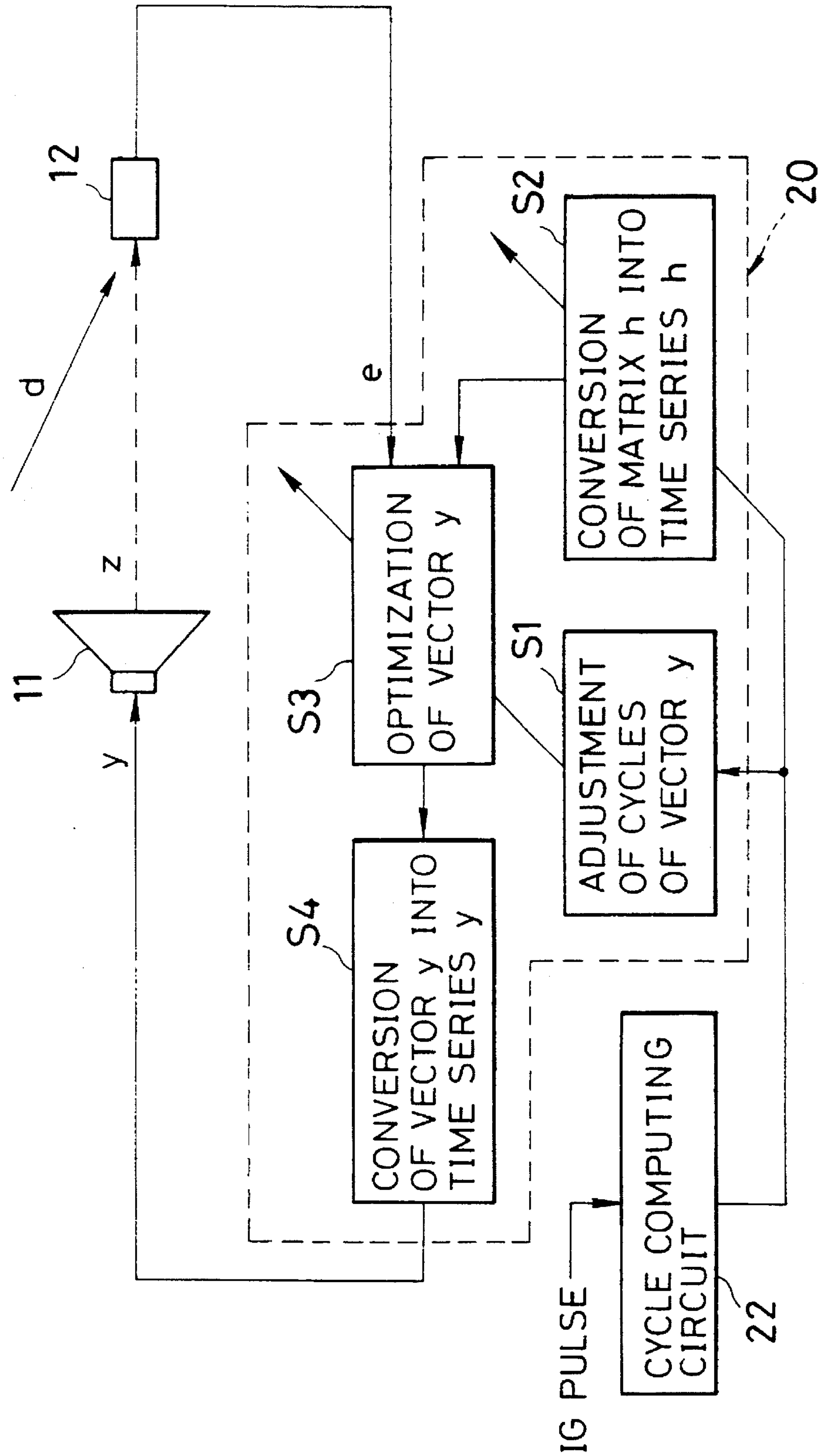
FIG. 3 is a block diagram showing a control system for optimizing the second vibrations.

In FIG. 3, the control section 20 is shown to have only one speaker 11 and microphone 12 for brevity of explanation. The control section 20 is so adapted as to adjust a cycle of a vector y of an input signal y to be generated to the speaker 11 on the basis of the input result of entry from the cycle computing circuit 22, at step S1, and a matrix h of an impulse response h indicative of a transmission characteristic between the microphone 12 and the speaker 11 is converted into a time series h by the microprocessor built in the control section 20, at step S2.

Then, the processor of the control section 20 optimizes the vector y sequentially on the basis of the time series h of the impulse response h and an output signal e, entered from the microphone 12, at step S3, and then converts the vector y into the time series U and generates the input signal U to the speaker 11, at step S4.

The speaker 11 reproduces the input signal y as anti-noises Z, and the microphone 12 detects the noises with their vibration energy reduced by deadening the noises d by the anti-noises Z and generates the digital output signal e to the processor built in the control section 20.

The processor of the control section 20 repeats the processing at steps S3 and S4, thereby sequentially optimizing the vector y of the input signal U and setting the vector y of the input signal y until the value of the output signal e becomes zero.

Then, a description will be made of the computation of the algorithm to be conducted at the above steps by the control section 20.

First, a sampling cycle of the output signal e from the microphone 12 is set as Δt. Supposing that the impulse response h functioning as the transmission characteristic between the microphone 12 and the speaker 11 is converged to zero within a limited period of time jΔt, the relationship among the noises d functioning as the first vibrations generated from the engine 8, the anti-noises Z functioning as the second vibrations generated from the speaker 11 when the input signal y to be generated to the speaker 11 is given, and a kth-sample value e(k) of the output signal e at the time k can be represented by the following formula (1):

$$e(k)=d(k)+Z(k)=d(k)+\text{matrix } h^T \times \text{matrix } y(k) \quad (1)$$

where matrix $h=[h_0\ h_1\ h_2\ \ldots\ h_{J-1}]^T$;

matrix $y(k)=[y(k)\ y(k-1)\ y(k-2)\ \ldots\ y(k-J+1)]^T$;

d(k) is a component of the noises d contained in e(k);

Z(k) is a component of the anti-noises Z contained in e(k); and y(k) is a value of the kth sample of the input signal y; wherein a value of the impulse response h after the elapse of the period of time jΔt after the impulse input is set as $h_j$.

Therefore, Z(k) in the formula (1) above can be rewritten by the formula (2):

$$Z(k) = \text{matrix } h^T \times \text{matrix } y(k) \quad (2)$$

$$= [h_0\ h_1\ h_2 \ldots h_{J-1}]^T \begin{bmatrix} y(k) \\ y(k-1) \\ y(k-2) \\ \ldots \\ y(k-J+1) \end{bmatrix}^T$$

$$= \sum_{j=0}^{J-1} h_j y(k-j)$$

As the noises d are periodic noises having a cycle NΔt, the anti-noises Z and the input signals y should be periodic noises and periodic signals, respectively, each having the same cycles NΔt as the noises d.

Therefore, the input signals y can give the following formula (3):

$$y(k) = y(k-qN) = y(k) \quad (3)$$
$$y(k-1) = y(k-qN-1) = y(k+N-1)$$
$$y(k-2) = y(k-qN-2) = y(k+N-2)$$
$$\ldots$$
$$y(k-N+1) = y(k-(q+1)N+1) = y(k+1)$$
where $q = 0, 1, 2, \ldots$ Thus, the formula (1) can be rewritten into formula (4) as follows:

$$e(k) = d(k) + \text{matrix } h^T \times \text{time series } y(k)$$
where time series $y(k) = [y(K)\ y(K+N-1)\ y(K+N-2) \ldots y(K+1)]^T$ $$\text{vector } h = \begin{bmatrix} h_0 + h_N + \ldots + h_{QN} \\ h_1 + h_{N+1} + \ldots + h_{QN+1} \\ \ldots \\ h_{J-QN-1} + h_{J-(Q-1)N-1} + \ldots + h_{J-1} \\ h_{J-QN} + h_{J-(Q-1)N} + \ldots + 0 \\ \ldots \\ h_{N-1} + h_{2N-1} + \ldots + 0 \end{bmatrix}$$

$$= [\bar{h}_0 + \bar{h}_1 + \bar{h}_2 + \ldots \bar{h}_{N-1}]^T$$

where

Q is a minimal value of an integer Q satisfying $J \leqq (q+1)N$.

Then, the sample value e(K+1) of a (K+i)th sample (where i=1, 2, . . . ) of the output signal e at the time k+i that has elapsed by the period of time i from the time k can be represented by the formula (5) as follows:

$$e(k+i) = d(k+i) + \text{vector } h^T \times \text{time series } y(k+i) \quad (5)$$
$$= d(k+i) + \text{time series } h(i)^T \times \text{time series } y(k)$$

where 6p1 time series y(k+i)=[y(k+i') y(k+i'−1) y(k+N−1) y(k+N−2) . . . y(k+i'+1)]$^T$ time series h(i)=[bar $h_i$, bar $h_{i'+1}$ . . . bar $h_{N+1}$ bar $h_0$ bar $h_1$ . . . bar $h_{i'-1}$]$^T$ wherein i' is the integral residue when i is divided by N.

In the formula (5) above, k represents merely an arbitrarily initial time of the input signal e. By replacing k with zero and replacing i with k, the formula (5) can be written as formula (6) as follows:

e(k)=d(k)+time series h(k)$^T$×time series y(0) =d(k)+time series h(k)$^T$×vector y where vector y=[y(0) y(N−1) y(N−2) . . . y(1)]$^T$=[$y_0$ $y_{N-1}$ $y_{N-2}$ . . . $y_1$]$^T$ The introduction of the following evaluation function into the above formula gives formula (7) as follows:

F=E]e(k)$^2$]

=E[d(k)+time series h(k)$^T$×vector y]

=E[d(k)$^2$]+2 vector y$^T$×E[d(k)×time series h(k)]+vector y$^T$×E[time series h(k)×time series h(k)$^T$]vector y where E[] represents an expectation value, in which symbol E is an expectation operator.

The formula (7) above gives the gradient with respect to the vector y of the evaluation function, as is given by formula (8) as follows:

$$\theta F/\theta \text{vector } y = 2E[d(k) \times \text{time series } h(k)] + 2E[\text{time series } h(k) \times \text{time series } h(k)^T]\text{vector } y \quad (8)$$
$$= 2E[\text{time series } h(k)\{d(k) + \text{time series } h(k)^T \text{ vector } y\}]$$
$$= 2E[\text{time series } h(k) \times e(k)]$$

When the time series h(k)×e(K) is employed as an instantaneous estimate for E[time series h(k)×e(K)], the value of the vector y which is the vector of the output signal to be generated to the speaker, having the cycle NΔt (where N=number of elements) giving the minimal value of F, can be optimized by repeating the computations of the following formula (9) on the basis of the steepest descent method.

$$\text{vector } y(K+1) = \text{vector } y(k) - \mu \times e(k) \times \text{time series } h(k) \quad (9)$$

where μ/2 is s convergence coefficient.

However, the formula (9) above can be replaced with a more simplified algorithm, as will be indicated below, when the processor functioning as the data processing device built in the control section 20 corrects the setting of the vibration energy of the anti-noises for reducing the vibration energy of the noises.

First, when a pair of the speaker 11 and the microphone 12 are employed, the formula (9) is replaced with formula (10) as follows:

$$y_{(k-j+QN)'}(k+1) = i\ y_{(k-j+QN)'} \times (k) - \mu \times e(k) \times h_j$$

At this time, the processor executes, for example, the following four operations at the time k.

Operation 1: To generate of a signal $y_{k'}$(k) to the speaker 11

Operation 2: To enter a signal e(K) from the microphone 12

Operation 3: To set an integer to N, the integer being closest to the product obtained by multiplying the rotational cycle of the engine 8, entered from the cycle computing circuit 22, with Ord/Δt or 1/(Ord×Δt)

Operation 4: To compute formula (10) with respect to j=0, 1, 2, . . . , J−1

In the formula (10) above, k' and (k−j+QN)' are the integral residues obtained by dividing k and (k−j+QN) with N, respectively, and reference symbol "Ord" is an arbitrary constant integer for setting the minimal degree of the reducing noises relative to the number of engine revolutions.

Then, when there are employed plural speakers 11 and microphones 12, an optimal value of the vector $y_1$ functioning as the vector of the signals to be generated to the first speaker for minimizing the evaluation function $$F = E\left[\sum_{m=1}^{M} e_m(k)^2\right]$$

can be given by repeating the computations of the following formula (11)

$$\text{vector } y_L(k+1) = \text{vector } y_L(k) - \mu \sum_{m=1}^{M} e_m(k) \times \text{time series } h_{Lm}(k) \quad (11)$$

for example, when $$\sum_{m=1}^{M} \text{time series } h_{Lm}(k) \times e_m(k)$$

is employed as an instantaneous estimate value for $$E\left[\sum_{m=1}^{M} \text{time series } h_{Lm}(k) \times e_m(k)\right]$$

on the basis of the steepest descent method; wherein:

$y_{1k}$: signal to be generated to the first speaker at time k;

$e_m$: signal to be entered from the mth microphone;

$h_{lmj}$: value in time jΔt after impulse response between the first speaker and the mth microphone;

L: number of the speakers;

M: number of the microphones; and

J: an integer indicating the convergence to zero of the impulse response between all the speakers and microphones within the limited time Δt;

$$\text{vector } y_I = [y_{I0}\ y_{IN-1}\ y_{IN-2} \ldots y_{II}]^T$$

$$\text{time series } h_{lm}(k) = [\text{bar } h_{lmk'}\ \text{bar } h_{lmk'-1} \ldots \text{bar } h_{lm0}\ \text{bar } h_{lm1} \ldots \text{bar } h_{lmk'+1}]^T$$

where $$\text{bar } h_{lm0} = h_{lm0} + h_{lmN} + \ldots h_{lmQN}$$

$$\text{bar } h_{lm1} = h_{lm1} + h_{lmN+1} + \ldots h_{lmQN+1}$$

$$\text{bar } h_{lmj-QN-1} = h_{lmj-QN-1} + h_{lmj-(Q-1)N-1} + \ldots + h_{lmJ-1}$$

$$\text{bar } h_{lmj-QN} = h_{lmj-QN} + h_{lmj-(Q-1)N} + \ldots + 0$$

$$\text{bar } h_{lmN-1} = h_{lmN-1} + h_{lm2N-1} + \ldots + 0$$

Thus, the formula (9) above can be rewritten as formula (12) as follows:

$$y_{L(k-j+QN)'}(k+1) = y_{L(k-j+QN)'}(k) - \mu \sum_{m=1}^{M} e_m(k) \times h_{Lmj} \quad (12)$$

At this time, the processor executes, for example, the following four operations at the time k.

Operation 11: To generate signals $y_{1k'(k)}$, $y_{2k'}(k)$, . . . , $y_{LK'}(k)$ to the first, second, . . . , Lth speakers Operation 12: To enter signals $e_1(k)$, $e_2(k)$, . . . , $e_M(k)$ from the first, second, . . . , Mth microphones Operation 13: To set an integer to N, the integer closest to the product obtained by multiplying the rotational cycle of the engine 8, entered from the cycle computing circuit 22, with Ord/Δt or 1/(Ord×Δt)

Operation 14: To compute formula (12) with respect to l=1, 2, . . . , L and j=0, 1, 2, . . . , J−1

In instances where the plural speakers 11 and the microphones 12 are employed, the optimal value of the vector $y_1$ can be given by repeating the computations of the following formula (13)

$$\text{vector } y_1(k+1) = \text{vector } y_1(k) - \mu \times a \times \text{time series } h_{lk''}(k) \times e_{k''}(k)$$

when a×time series $h_{lk'}(k) \times e_{k'}$, is used as an instantaneous estimate value for $$E\left[\sum_{m=1}^{M} \text{time series } h_{Lm}(k) \times e_m(k)\right]$$

a vector $y_1$ being the vector of the signals to be generated to the first speaker for minimizing the evaluation function $$F = E\left[\sum_{m=1}^{M} e_m(k)^2\right]$$

where k" is a value obtained by dividing k with M and by adding one to the resulting quotient; and a is a constant. The formula (13) can be computed in a time shorter than the formula (11).

Hence, the formula (9) can be replaced with formula (14) as follows:

$$y_{l(k-j+QN)'}(k+1) = y_{l(k-j+QN)'}(k) - \mu \times a \times e_k(k) \times h_{lk''j}$$

At this time, the processor executes, for example, the following four operations at the time k.

'Operation 21: To generate signals $y_{1k'}(k)$, $y_{2k'}(k)$, . . . , $y_{Lk'}(k)$ to the first, second, . . . , Lth speakers Operation 22: To enter signals $e_{k''}(k)$ from the k"-th microphone Operation 23: To set an integer to N, the integer being closest to the product obtained by multiplying the rotational cycle of the engine 8, entered from the cycle computing circuit 22, with Ord/Δt or 1/(Ord×Δt)

Operation 24: To compute formula (14) with respect to l=1, 2, . . . , L and j=0, 1, 2, . . . , J−1

Therefore, the algorithm can be computed merely by repeating the computations of the formulas (9), (11) and (12) or their simplified formulas (10), (12) and (14), thereby shortening the computation time for controlling the entry into the speakers.

Correction of Data Length At A Transient Time (Insertion or Deletion of Data Value)

Basic Examples (FIGS. 4–10)

Figure 4:
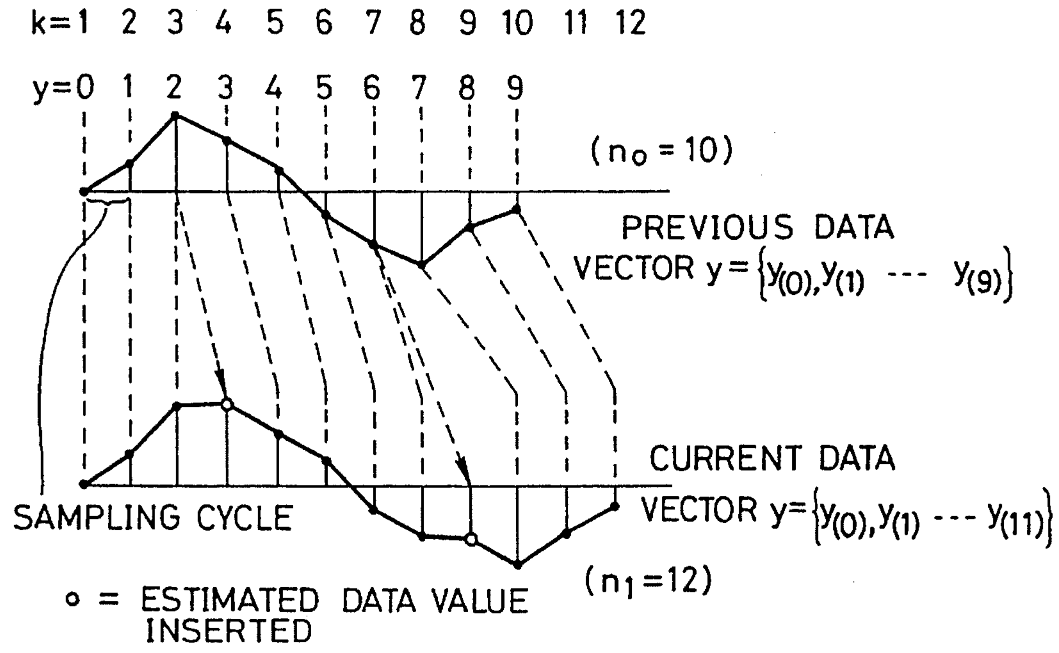
FIG. 4 is a schematic representation showing an example of lengthening the data length of data of the vibrations by inserting estimated data values.

With reference to FIGS. 4 et seq, a description will be made of the correction of the second vibrations during the transient time during which the rotational cycle of the engine 8 varies by acceleration or deceleration. This correction is executed before the optimization process at step S3 for optimizing the vector y as shown in FIG. 3.

Figure 5:
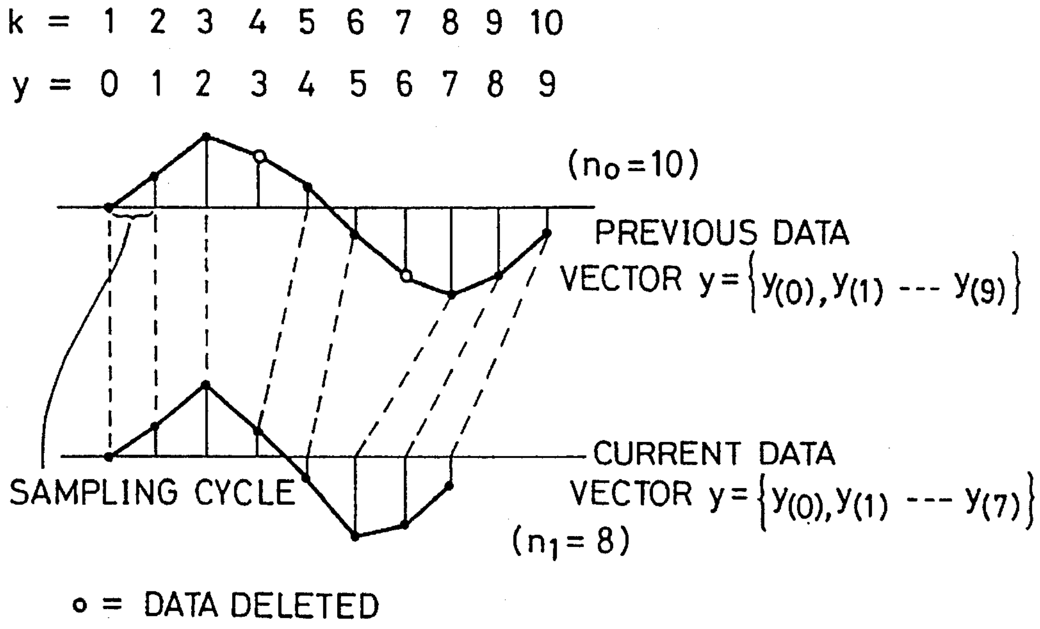
FIG. 5 is a schematic representation showing an example of shortening the data length of data of the vibrations by deleting a data value.

FIGS. 4–5 diagrammatically illustrate the ways of adjusting the data lengths of the data value. FIG. 4 is directed to the correction for lengthening the data length by one cycle portion, i.e. increasing the number of data, and FIG. 5 is directed to the correction for shortening the data length by one cycle portion, i.e. decreasing the number of data.

At the upper side of FIG. 4, the previous data of the second vibrations optimized in the manner as described hereinabove is shown. The values set at every sampling timing, as indicated by black circles, indicate the vibration energies of the second vibrations. The second vibrations corresponding to one cycle portion to be generated from the speaker may be represented by the vibration wave form corresponding to the wave form obtained by connecting the two adjacent black circles. FIG. 4 illustrates the previous data having the data number n0 of 10 and the current data having the data number increased to the data number n1 of 12 from the previous data, a current data being such that its data length is currently set so as to correspond to the cycles varied with the number of engine revolutions. In this case, two estimated data values are inserted into the previous data in order to comply with the current data and they are indicated by white circles.

On the other hand, FIG. 5 illustrates the current data created by shortening the data length of the previous data to the contrary of the case as shown in FIG. 4. In this case, excessive two data values are deleted from the previous data and indicated by white circles.

Figure 6:
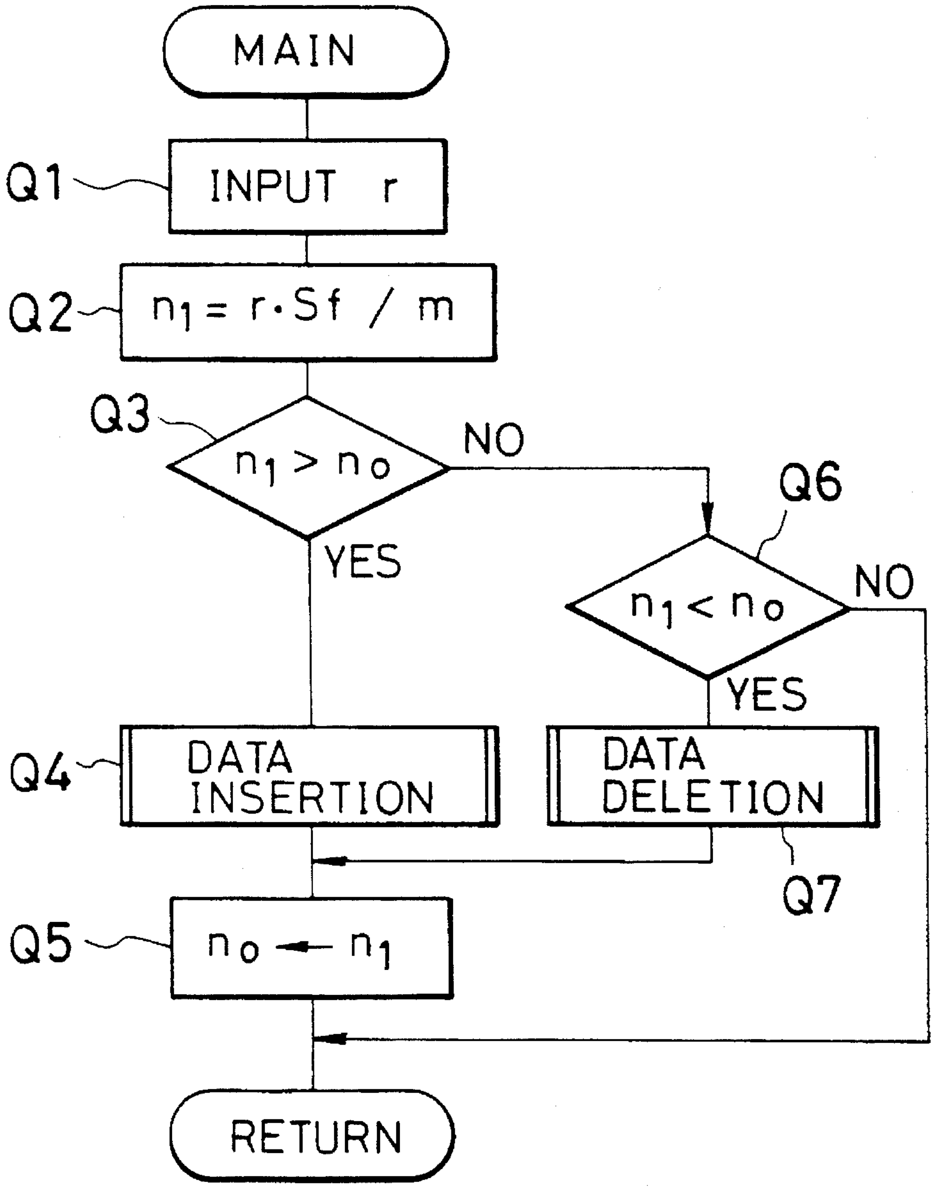
FIG. 6 is a flowchart showing an example of control for correcting the data length of the data of the second vibrations.
Figure 7:
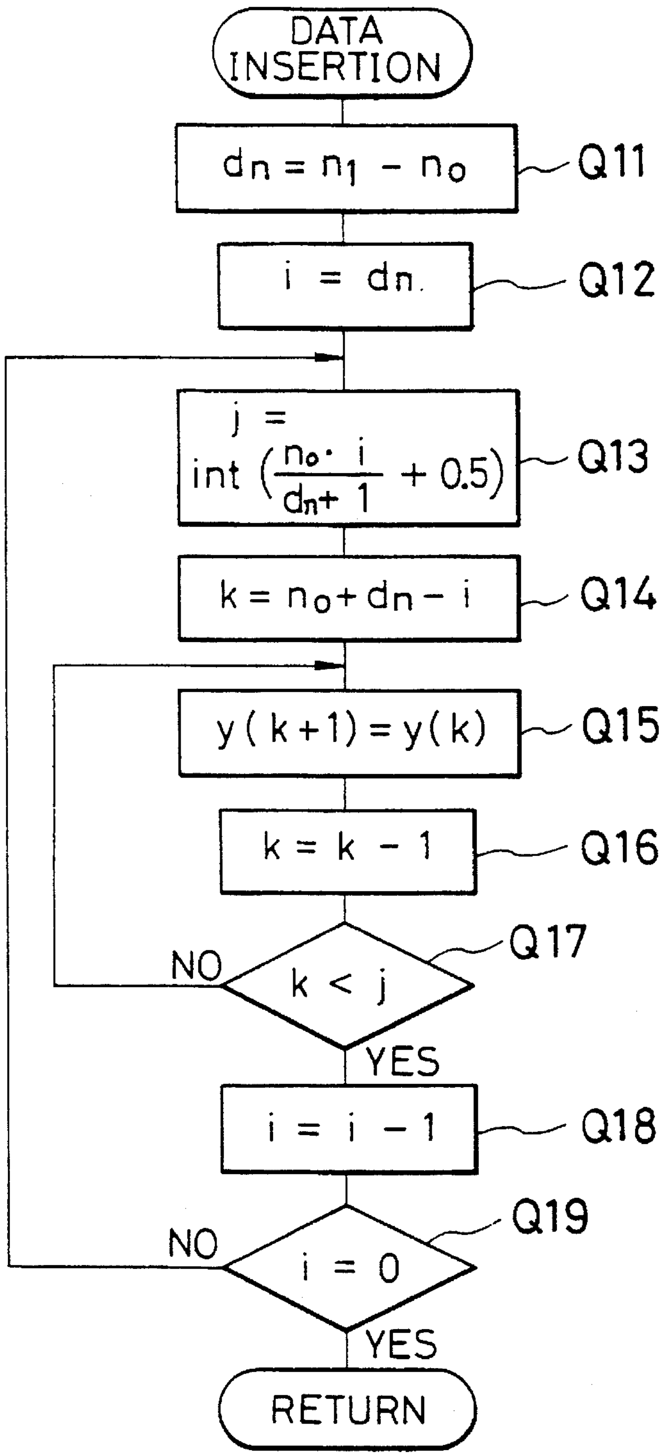
FIG. 7 is a flowchart showing an example of lengthening the data length of the data of the second vibrations.
Figure 8:
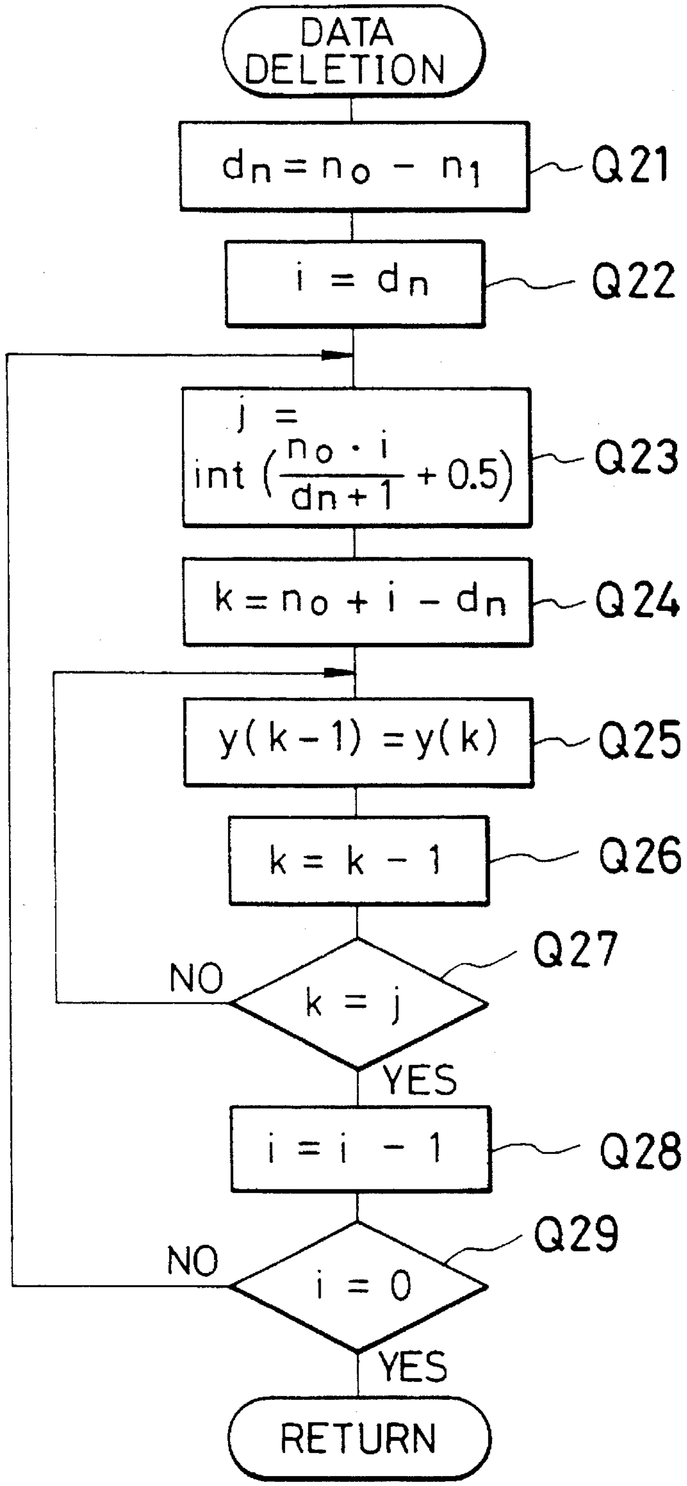
FIG. 8 is a flowchart showing an example of shortening the data length of the data of the second vibrations.

FIGS. 6–8 illustrate the flow charts showing the instances in which the data length is corrected by insertion or deletion of the number of the data during the transient period of time during which the number of engine revolutions varies.

In the main flowchart as shown in FIG. 6, an IG pulse cycle r (in seconds) is entered at step Q1. Then, at step Q2, the data number n1 of the current data to be currently set is computed on the basis of the equation, as indicated at step Q2, wherein Sf is a sampling frequency (Hz) and m is an integer.

At step Q3, it is decided to determine if the data number n1 of the current data is larger than the data number n0 of the previous data. When the result of this decision indicates that the data number n1 of the current data is larger than the data number n0 of the previous data, then the program flow goes to step Q4 at which the previous data is corrected by inserting the estimated data values into the previous data in a manner as will be described hereinafter. Then, at step Q5, the data number n0 of the previous data is updated by the data number n1 of the current data.

On the other hand, when it is decided at step Q3 that the data number n1 of the current data is not larger than the data number n0 of the previous data, then the program flow goes to step Q6 at which it is further decided to determine if the data number n1 of the current data is smaller than the data number n0 of the previous data. When the result of decision at step Q6 indicates that the data number n1 of the current data is smaller than the data number n0 of the previous data, the program flow is followed by processing for the deletion of the unnecessary data number in a manner as will be described hereinafter and then proceeding to step Q5.

If the decision at step Q6 gives the negative result that the current data number n1 is not smaller than the previous data number n0, the program flow is returned as it is because the correction of the data by inserting or deleting is not required, and the processing for optimization as described hereinabove is executed.

FIG. 7 shows the contents of the processing for the data insertion to be executed at step Q4 in FIG. 6. In the example as indicated in FIG. 7, the estimated data values are inserted into the previous data at equal intervals and the estimated data value is set to the data value located immediately ahead of the position in which the estimated data value is inserted.

Given the foregoing, the number of estimated data values, dn, to be inserted currently, is computed by subtracting the number of the previous data, n0, from the number of the current data, n1, at step Q11. Then, at step Q12, the number dn of the estimated data values to be inserted is set as i, followed by step Q13 at which the position in which the estimated data value is to be inserted is set by the equation $$j=\text{int}]n0\times i/(dn+1)+0.5]$$

where symbol "int" means rounding the result of computation to the nearest whole number.

The symbol "j" indicates the position in which the estimated data value is to be inserted. For example, as shown in FIG. 4, when n0=10, n1=12 and i=dn=2, the computation of the portion, enclosed by parentheses, gives 7.166 . . . so that this computation result is rounded to j=7.

Then, at step Q14, k is set by the equation k=n0+dn–i. As the number of the previous data, n0, is 10 in this example, k is shown such that the data is located in the right end position in FIG. 4. Thereafter, at step Q15, the position of the data value corresponding to y(k) in the previous data is set as the position of the data value corresponding to y(k+1) in the current data, followed by proceeding to step Q16 at which k is set to k–1. Then, at step Q17, it is decided to determine if k is smaller than j. When this decision gives the negative result, then the program flow is returned to step Q15.

On the other hand, when it is decided at step Q17 that k is smaller than j, the program flow goes to step Q18 at which a value obtained by subtracting one from i is set as i and then to step Q19 at which it is decided to determine if i is zero. If the result of this decision indicates that i is not zero, then the program flow is returned to step Q13.

At the time when the decision at step Q19 gives the result that i is zero, it is determined that the insertion of the estimated data value for creating the current data has been finished.

In the case of FIG. 4, the result of the decision at step Q19 indicates that i becomes zero at the time when the processes at steps 13–18 have been repeated twice, thereby yielding the current data having the data length corresponding to the cycle detected currently at the lower side of FIG. 4.

Figure 9:
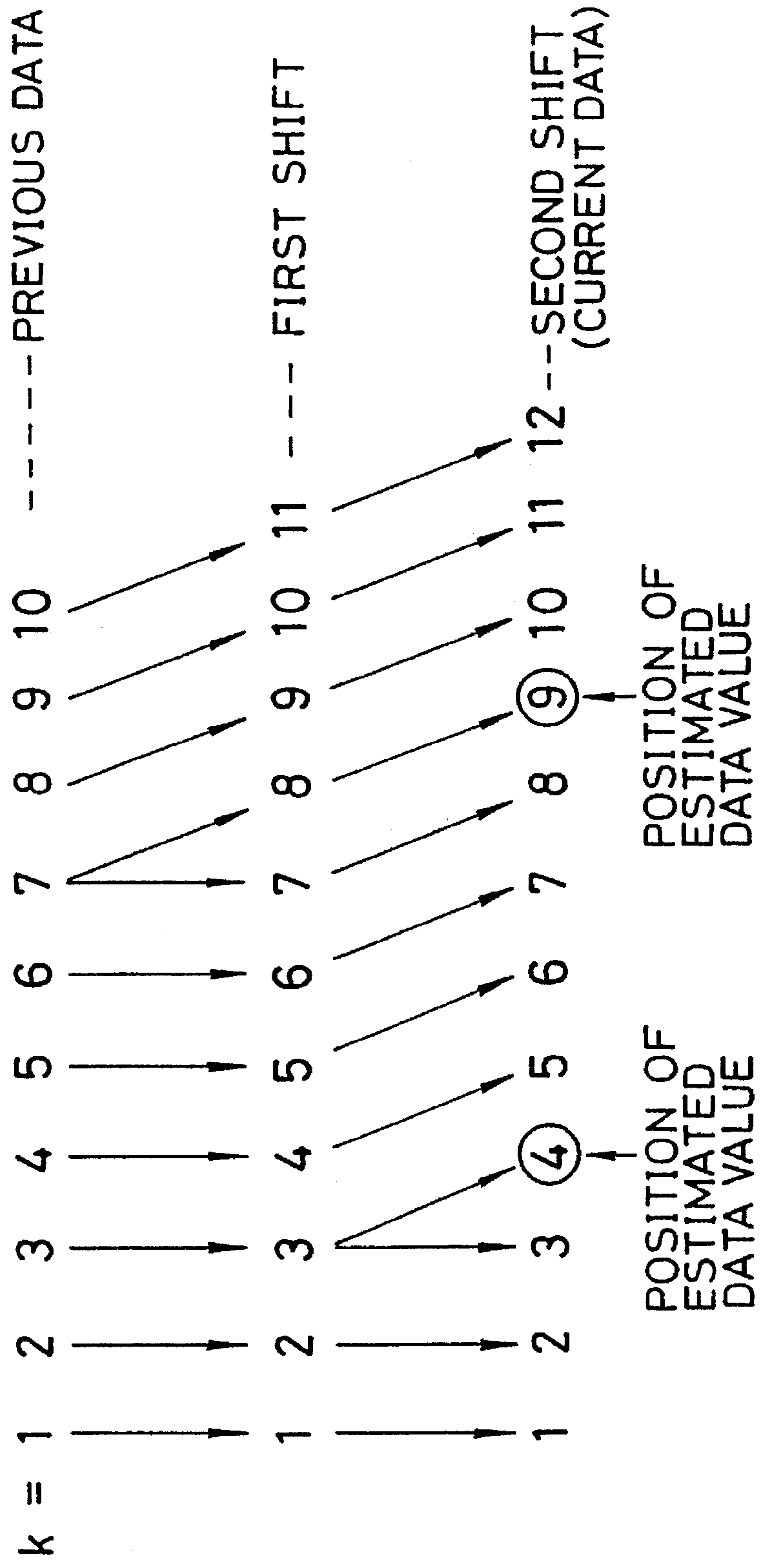
FIG. 9 is a schematic representation showing an example of control for FIG. 7.

FIG. 9 diagrammatically illustrates the modes of shifting the data values and setting the estimated data values with reference to the instances as shown in FIG. 4. The speaker 11 generates the wave form of the vibration corresponding to the current data with its data length adjusted in the fashion as indicated at the lower side of FIG. 4. Further, the estimated data value to be inserted may be set as the data value that is located immediately behind the position in which the estimated data value is to be inserted.

FIG. 8 indicates the details of the data deletion processing to be executed at step Q7 as shown in FIG. 6. In this example, the estimated data values are deleted from the previous data at equal intervals. The processing as shown in FIG. 8 corresponds in many respects to the processing for inserting the estimated data values as shown in FIG. 7. Hence, the processes different from the processing as shown in FIG. 7 will be described and a description of the identical processes will be omitted, for brevity of explanation.

Figure 10:
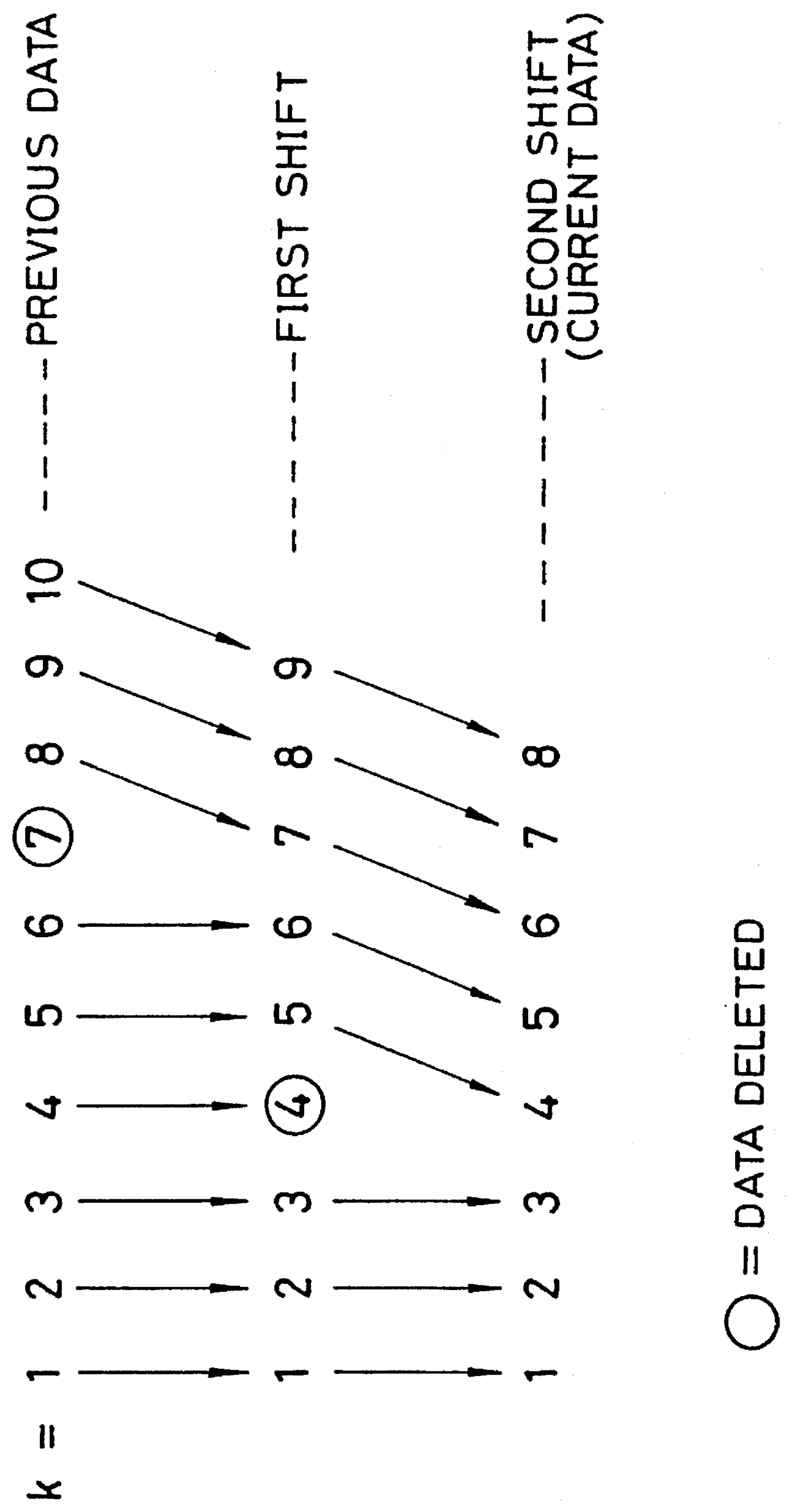
FIG. 10 is a schematic representation showing an example of control for FIG. 8.

First, the position of j to be set at step Q23 indicates the position from which the estimated data value is to be deleted. Further, the positions of the data values located behind the positions from which the data values are deleted are shifted forwards by the processing at steps Q25–Q27. FIG. 10 diagrammatically illustrates the mode of deleting the data values with reference to the instance as shown in FIG. 5.

Figure 11:
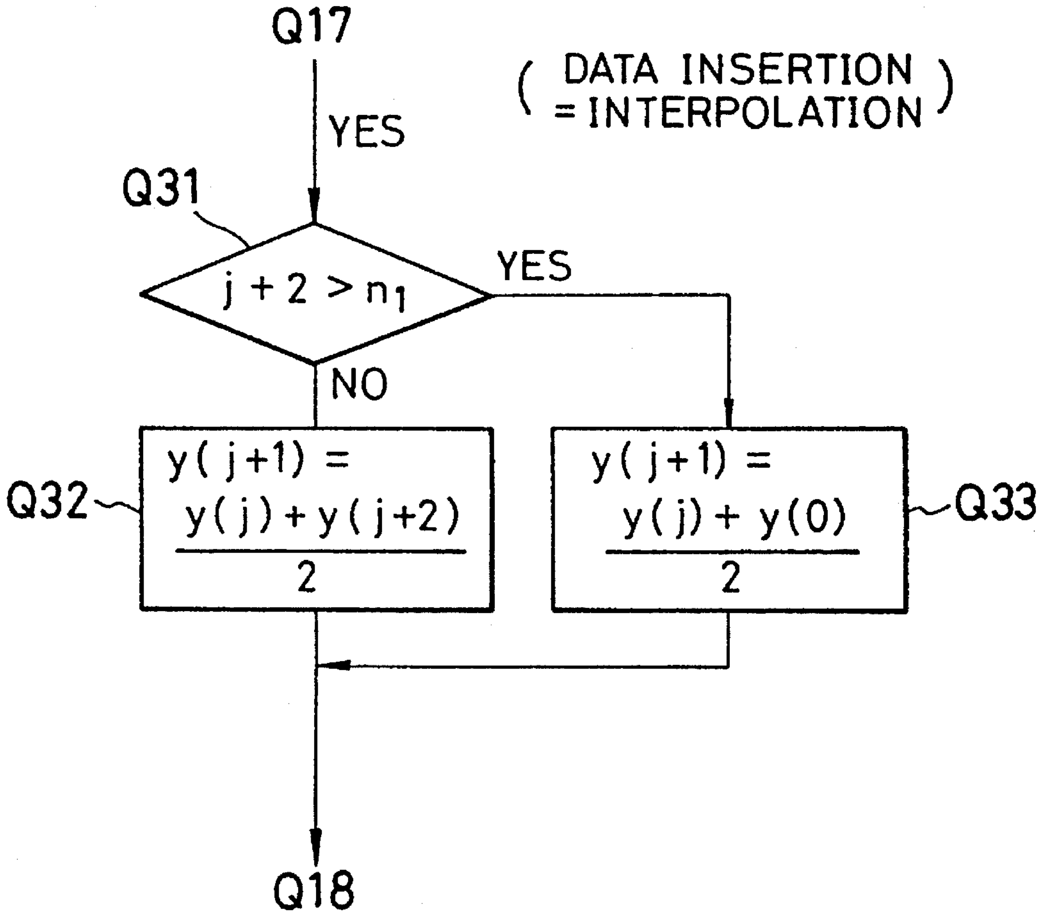
FIG. 11 is a flowchart showing an essential portion of another example of correction by lengthening the data length of the data of the second vibrations.

Variant Example 1 (FIGS. 11–12):

FIG. 11 illustrates an example in which the estimated data value is set by primary interpolation on the basis of the data values positioned ahead of and behind the position in which the estimated data value is to be inserted. In other words, in this example, the estimated data value is set as an arithmetic mean value of the data values located ahead of and behind the position in which it is to be inserted.

Specifically, FIG. 11 indicates the processing to be executed between steps Q17 and Q18 in FIG. 7. When it is decided at step Q17 that k is smaller than j, then the program flow goes to step Q31 at which it is further decided to determine if j+2 is larger than n1. On the other hand, when the result of decision at step Q31 indicates that j+2 is not larger than n1, then the arithmetic mean value of the data values located ahead of and behind the position in which the estimated data value is to be inserted is set as an estimated data value as indicated at step Q32. To the contrary, when it is decided at step Q31 that j+2 is larger than n1, it is shown that no data value exists in the position behind the position in which the estimated data value is to be inserted. At this time, the data value located in the position behind the position in which to insert the estimated data value corresponds to the first data value. Hence, at step Q33, an arithmetic mean value between the data value located in the position immediately ahead of the inserting position in which to insert the estimated data value and the data value located in the first position is set as an estimated data value.

Figure 12:
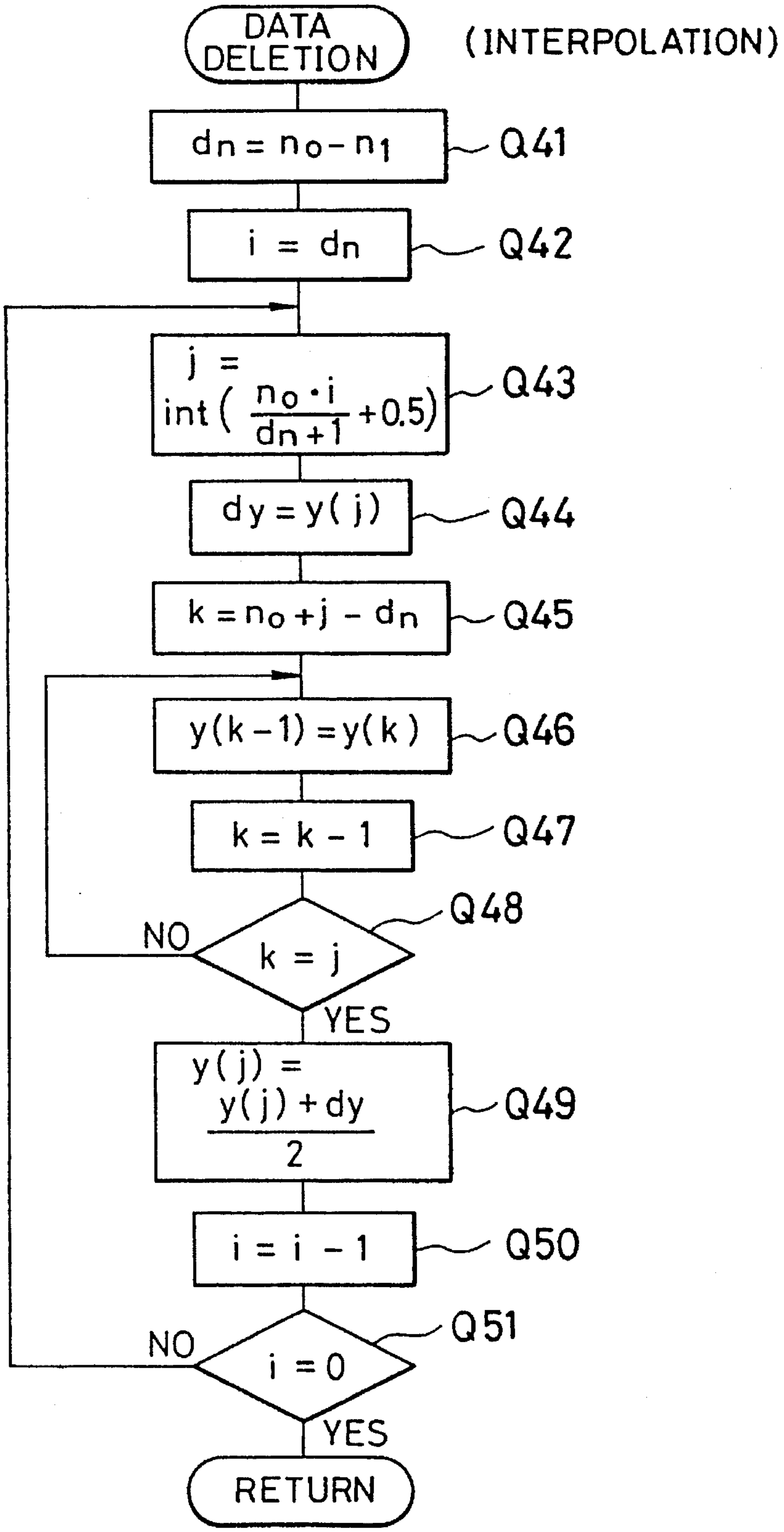
FIG. 12 is a flowchart showing another example of correction by shortening the data length of the data of the second vibrations.

On the other hand, FIG. 12 indicates an example in which the data value existing ahead of and behind the position in which the data value is to be deleted is subjected to primary interpolation. The processing as shown in FIG. 12 is basically equivalent to that of FIG. 8. Hence, the processes different from the processing as shown in FIG. 8 will be described and a description on the identical processes will be omitted, for brevity of explanation.

In FIG. 12, at step Q44 the data value existing in the position from which the data value is to be deleted is set as dy and, at step Q49, the data value is set as an arithmetic mean value between the data value dy and the data value existing in the position immediately behind the position from which the data value is to be deleted. It is also possible, as a matter of course, that an arithmetic mean value between the data value dy and the data value existing in the position immediately behind the position from which the data value is to be deleted is set as a data value existing in the position from which the data value has already been deleted.

Figure 13:
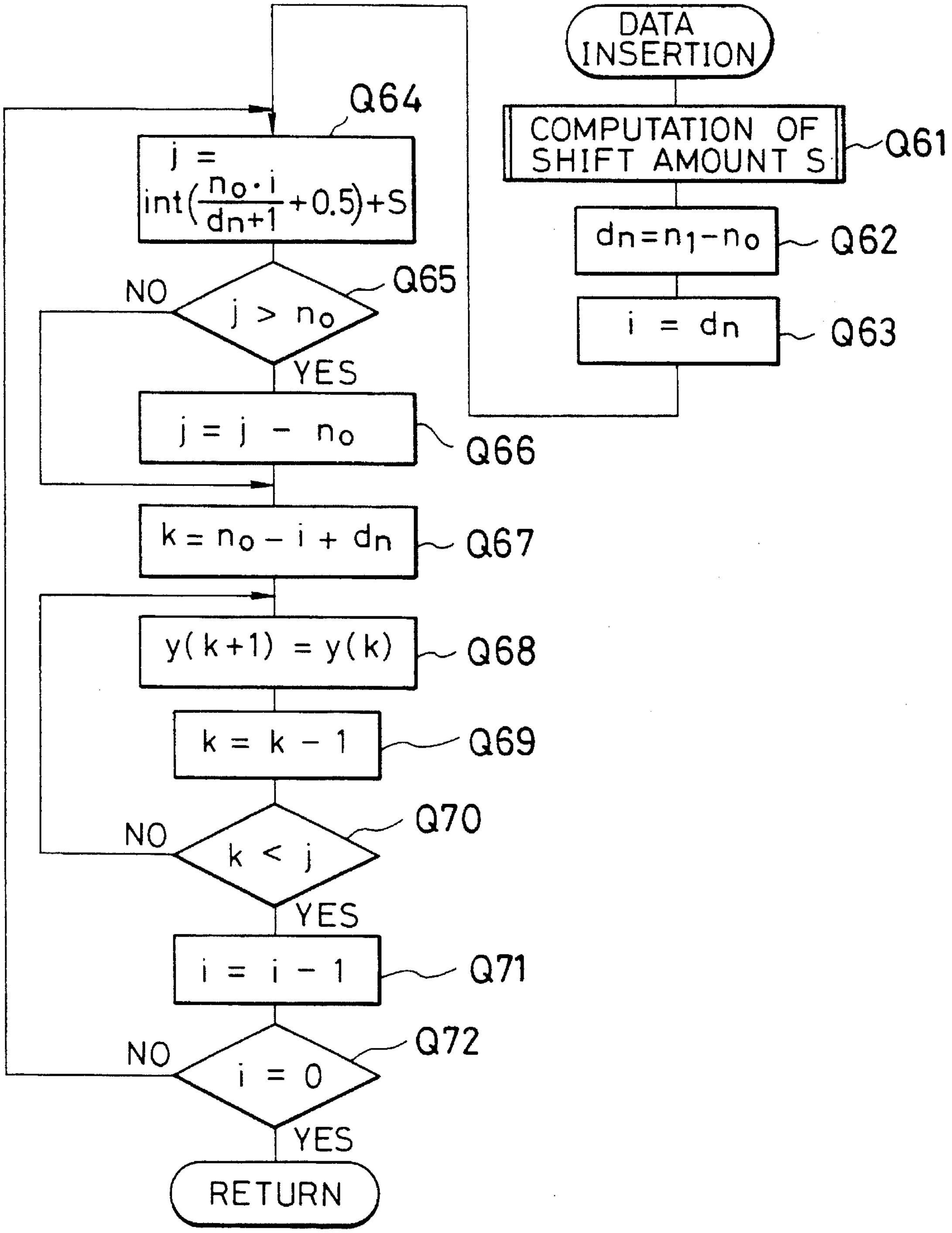
FIG. 13 is a flowchart showing a further example of correction by lengthening the data length of the second vibrations.

Variant Example 2 (FIGS. 13–16):

FIG. 13 indicates an example in which the position in which the estimated data value is inserted varies at every cycle.

In this example, the processing is executed in basically the same manner as the processing as shown in FIG. 7. Hence, the processes different from the processing as shown in FIG. 7 will be described and a description of the identical processes will be omitted, for brevity of explanation. In other words, a shift amount S (represented in an integer) of the position in which the estimated data value is inserted is set at step Q61, and the shift amount S is added in setting the inserting position j at step Q64. In order to prevent the data value from being inserted or deleted in the same position at every variation in cycle by setting the shift amount S, there are set processes at steps Q65 and Q66.

Figure 15:
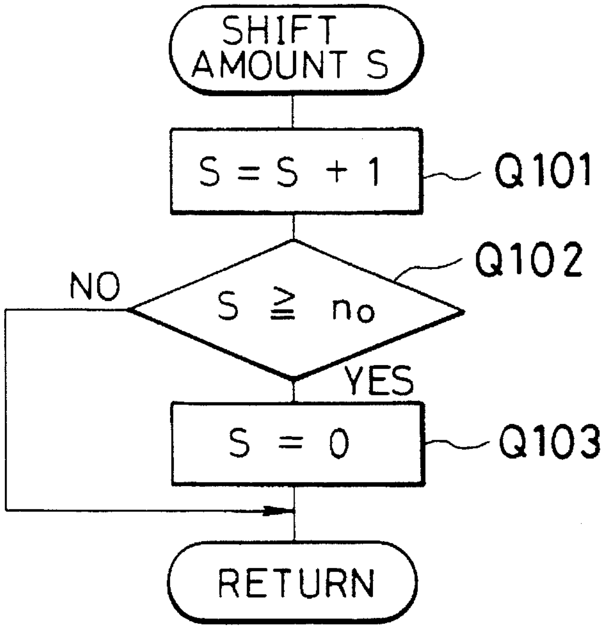
FIG. 15 is a flowchart showing an example of setting a shift amount S in FIGS. 13 and 14.
Figure 16:
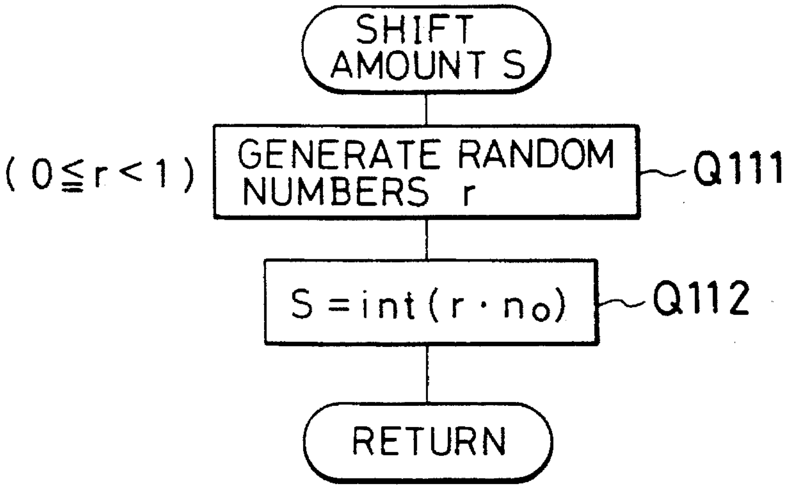
FIG. 16 is a flowchart showing another example of setting a shift amount S in FIGS. 13 and 14.

Specifically, the shift amount S may be set at step Q61 in a manner, for example, as shown in FIG. 15. FIG. 15 shows an example in which the inserting positions are shifted rearward sequentially by one position. FIG. 16 shows another example for setting the shift amount S at step Q61, in which the shift amount S is set on the basis of random numbers.

Figure 14:
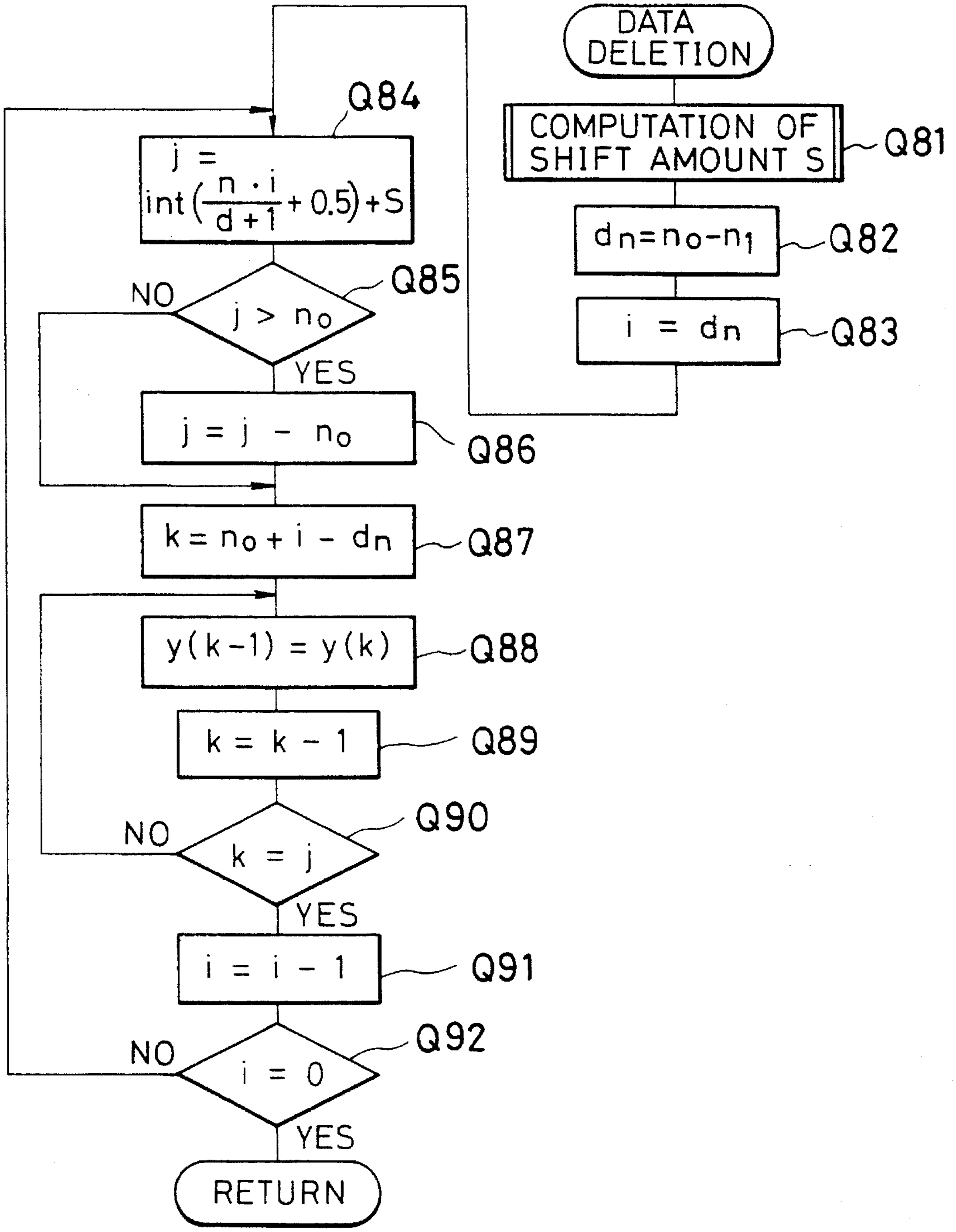
FIG. 14 is a flow chart showing a further example of correction by shortening the data length of the second vibrations.

FIG. 14 indicates an example in which the position from which the data value is deleted is shifted at every cycle on the basis of the shift amount S, in a manner like in FIG. 13. The processing as shown in FIG. 14 is basically the same as the processing as shown in FIG. 8 with the exception for processes at steps Q81 and Q84–86 (corresponding to processes at steps Q61 and Q64–66 in FIG. 13). Hence, a description of the processes steps Q81 and Q84–86 is omitted.

The arrangement of the control system as claimed in claim 4 or 8 can preferably reduce the vibrations to a sufficient extent by preventing the ability of storing the data values from being partially poor.

Further, the arrangement of the system as claimed in claim 5 or 7 can preferably reduce the vibrations to a sufficient level by ensuring reliability of the estimated data values and the data values existing in the positions ahead of and behind the position from which the data value is to be deleted.

Contraction or Extension of A Whole Wave Form of Second Vibrations in a Transient Period Basic Examples (FIGS. 17–21):

A description will be made of processing for extending or contracting a whole wave form of the second vibrations during a transient period of time during which the rotational cycle of the engine 8 varies, for example, by acceleration or deceleration, with reference to FIGS. 17 et seq. This processing is executed before the processing for optimization of the vector y at step S3 in FIG. 3.

Figure 17:
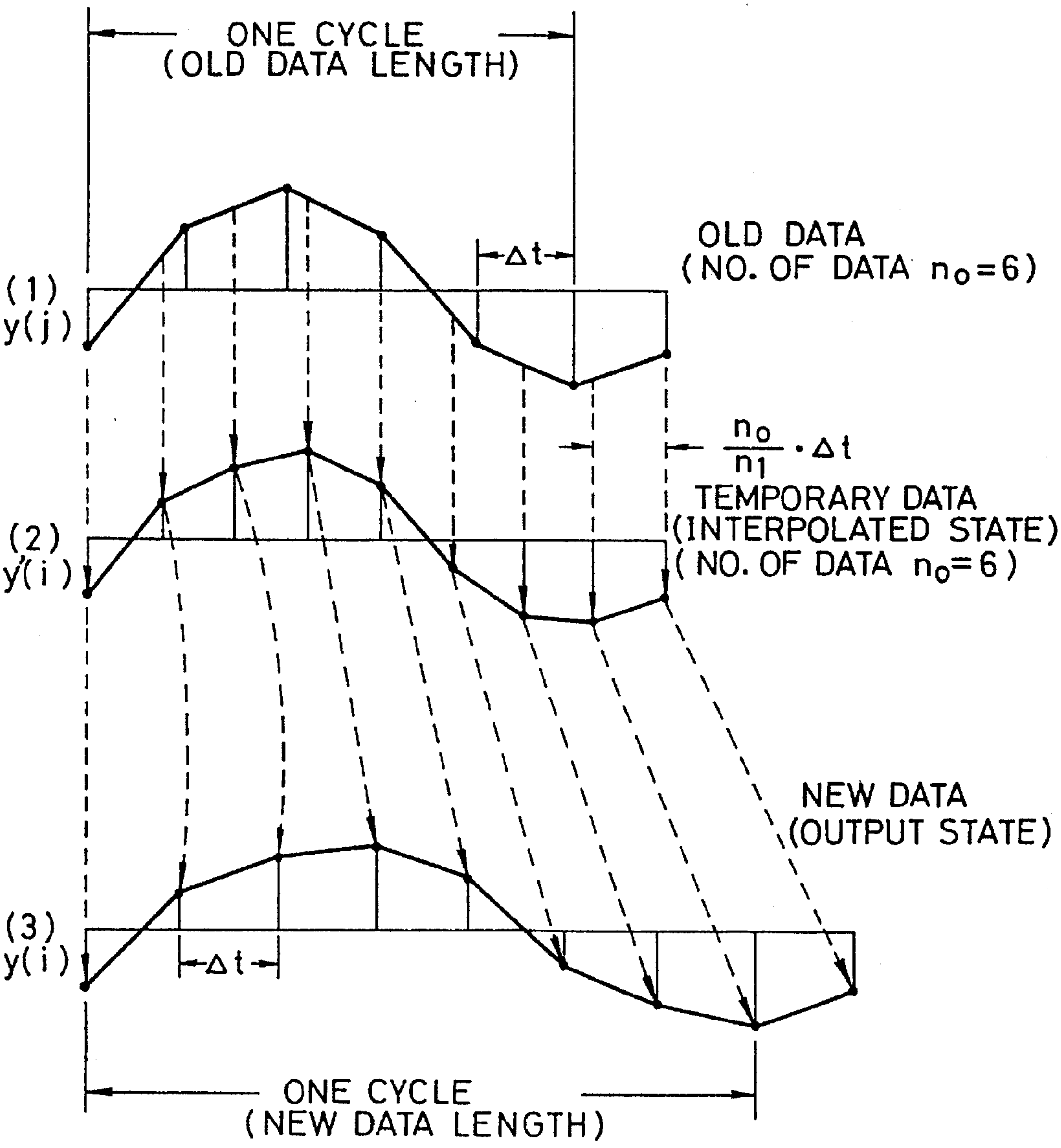
FIG. 17 is a schematic representation showing an example of extending the wave form as a whole by interpolation.

FIGS. 17–21 shows instances where the whole wave form of the second vibrations is extended or corrected by interpolation. The procedures of the interpolation are shown in FIG. 17. FIG. 17(1) indicates a wave form of the previous vibrations, having six data values, and FIG. 17(3) indicates a wave form of the current vibrations having eight data values, which are formed by extending the wave form of the previous vibrations. First, as shown in FIG. 17(2), a temporary wave form is created as having the same data length as the data length of the wave form of the previous vibrations, and a sampling cycle is set on the temporary data length in accordance with the new number of data values, i.e. eight data values. In this example, the temporary sampling cycle in the temporary data length (the temporary vibration wave form) is 6/8 of the sampling cycle in the basic or previous data length.

The data value in the previous vibration wave form is plotted on the temporary data length at every temporary sampling timing. By returning the temporary vibration wave form to its basic sampling cycle (in other words, by forming the temporary vibration wave form at every basic sampling cycle), the vibration wave form with the wave form extended is created in such a form as shown in FIG. 17(3). The vibration wave form can be contracted in substantially the same manner as described immediately hereinabove. In this case, the temporary sampling cycle is set to be larger than the basic sampling cycle.

FIGS. 18–21 show the flow charts for executing the interpolation as shown in FIG. 17.

Figure 18:
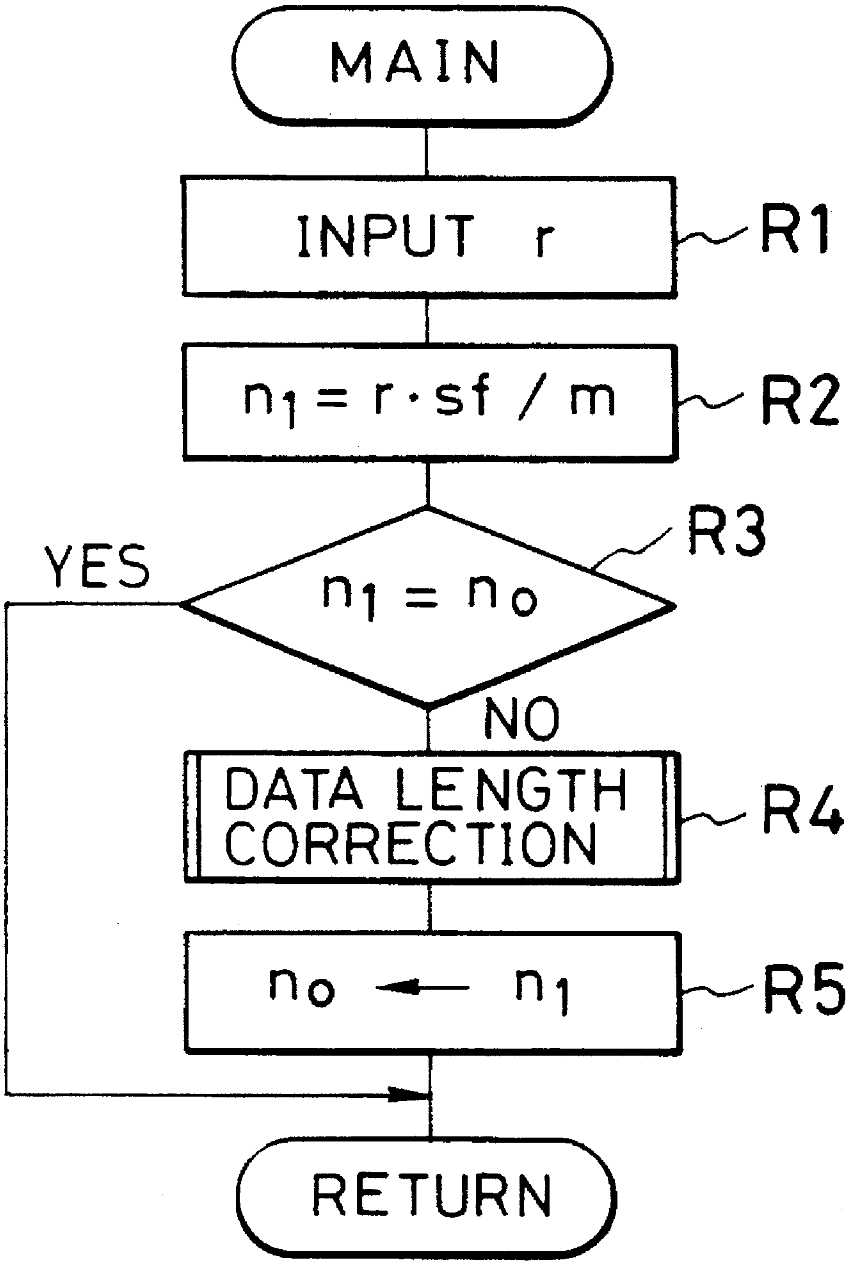
FIG. 18 is a flowchart for carrying out the interpolation of FIG. 17.

First, an IG pulse cycle r (represented in seconds) is read at step R1 in FIG. 18, followed by proceeding to step R2 at which the data number n1 to be set at this time is computed by formula $n1=r\times sf/m$, where sf is a sampling frequency (Hz) and m is an integer.

Then, at step R3, it is decided to determine if the data number n1 of the current data is equal to the data number n0 of the previous data. When the result of this decision indicates that the data number n1 of the current data is not equal to the data number n0 of the previous data, then the program flow goes to step R4 at which the interpolation is implemented in the manner as shown in FIG. 17, followed by updating the current data number n1 as the previous data number n0. On the other hand, when it is decided at step R3 that the data number n1 of the current data is equal to the data number n0 of the previous data, then the program flow is returned as it is because no interpolation for extending or contracting the vibration wave form is required, thereby executing the processing for optimization in the manner as shown in FIG. 3.

Figure 19:
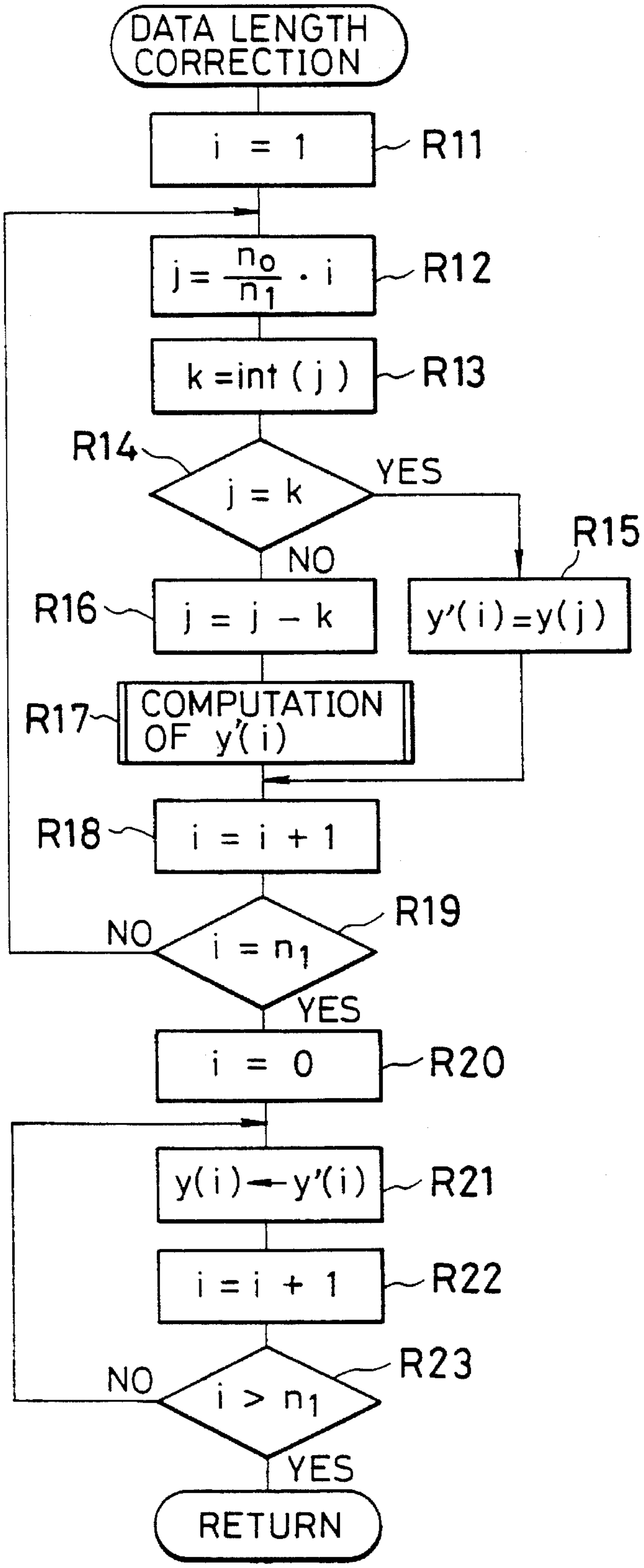
FIG. 19 is a flowchart for carrying out the interpolation of FIG. 17.

FIG. 19 indicates the contents of the processing to be executed at step R4 in FIG. 18. First, at step R11, i is set to 1, followed by proceeding to step R12 at which j is set by the formula $j=n0/n1\times i$. Then, at step R13, k is determined by the formula: k=int(j). The symbol "int" at step R13 means rounding the result of computation to the nearest whole number. In this example, where n0 is 6 and n1 is 8, the value enclosed by the parentheses is calculated to give k=8 because the initial value enclosed by the parentheses is 0.75.

Then, at step R14, it is decided to determine if j=k. When this decision gives the result that j=k, then the program flow goes to step R15 at which y(j) is set as y'(i), followed by proceeding to step R18. On the other hand, when the result of decision at step R14 indicates that j is not equal to k, the program flow goes to step R16 at which j is set to j-k and then to step R17 at which y'(i) is computed in a manner as will be described hereinafter, followed by proceeding to step R18. The processing at step R15 is so adapted as to deal with the instance where the previous data value exists in the phase position of j, while the processing at step R16 is so adapted as to deal with the instance where no previous data value exists in the phase position of j.

At step R18, i is set to i+1, followed by proceeding to step R19 at which it is decided to determine if i is equal to n1 corresponding to the current data number. When the result of this decision indicates that i is not equal to n1, then the program flow is returned to R12 at which the processing as described hereinabove is repeated and the interpolation is continued.

On the other hand, when the decision at step R19 gives the result that i is equal to n1 corresponding to the current data number, the program flow goes to step R20 at which i is set to zero and then to step R21 at which y'(i) is set to y(i). Thereafter, at step R22, i+1 is set to i, followed by proceeding to step R23 at which decision is made to determine if i is larger than n1. This decision is so set as to give the negative result at the initial stage, the processing at steps R21 et seq is repeated. Then, the interpolation is terminated at the time when the decision at step R23 gives the affirmative result that i is larger than n1, followed by the return of the program flow.

The processing at steps R12–19 is so adapted as to deal with the processing for creating the temporary data as shown in FIG. 17(2), and the processing at steps R20 et seq is so adapted as to deal with the processing for changing the temporary data of FIG. 17(2) into new data as shown in FIG. 17(3).

Figure 20:
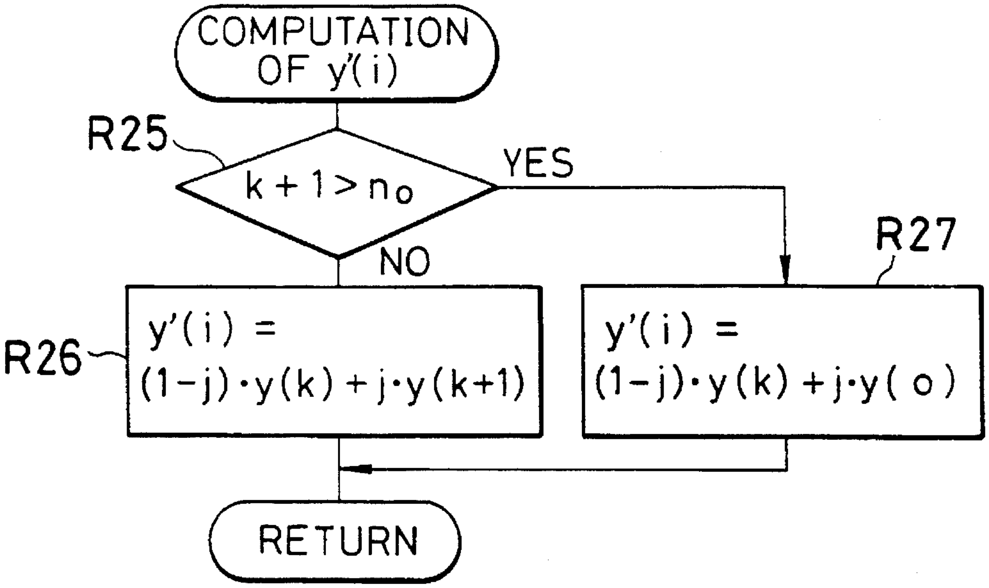
FIG. 20 is a flowchart for carrying out the interpolation of FIG. 17.
Figure 21:
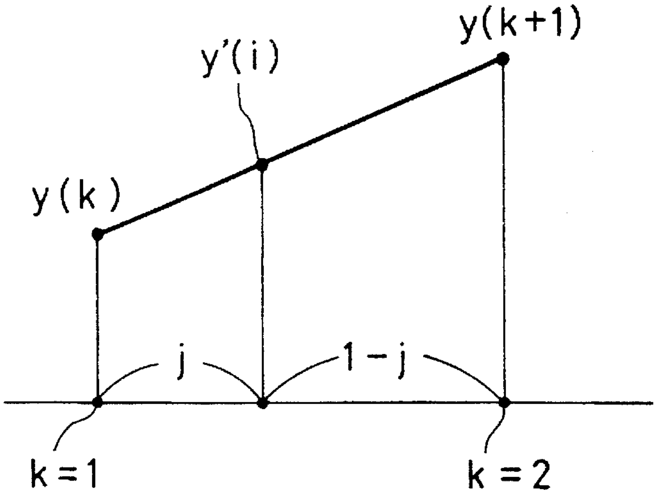
FIG. 21 is a schematic representation showing the contents of the flowchart for carrying out the interpolation of FIG. 20.

FIG. 20 shows the contents of the processing for the computation of y'(i) at step R17 in FIG. 19. At step R25 in FIG. 20, it is decided to determine if k+1 is larger than n0. When this decision gives the negative result that k+1 is equal to or smaller than n0, then the program flow goes to step R26 at which the arithmetic mean value of the values enclosing the phase position of i is set as y'(i) in order to execute the primary interpolation, followed by the return of the program flow. On the other hand, when the result of the decision at step R25 indicates that k+1 is larger than n0, then the program flow goes to step R27 at which the arithmetic mean value between the value of the first phase position and the value of the phase position immediately ahead is set as y'(i), because, although the phase position of k is located in the last position and no phase position behind it exists, the phase position thereafter is equal to the first phase position. FIG. 21 diagrammatically shows the meaning of the arithmetic mean as indicated by step R26 or R27, i.e. the contents of the primary interpolation.

Figure 24:
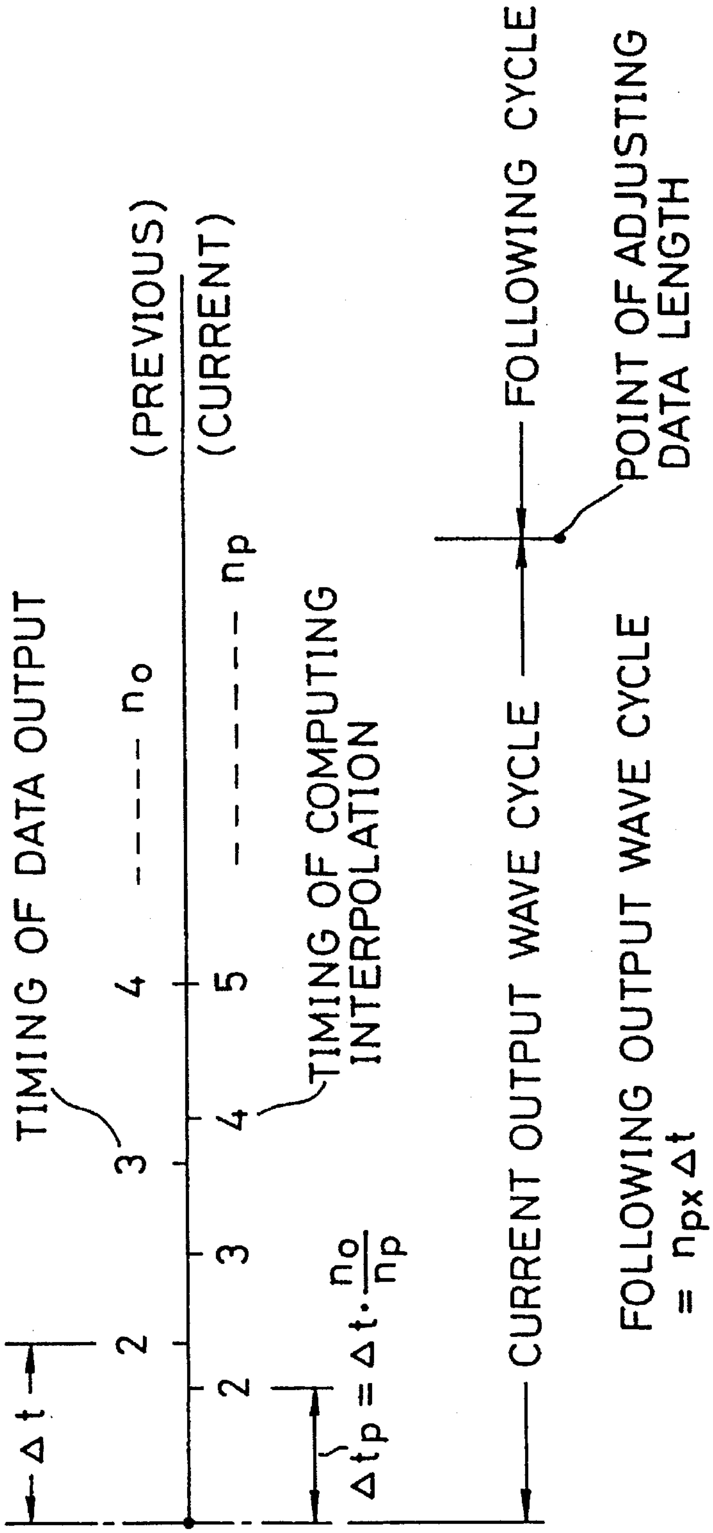
FIG. 24 is a schematic representation showing a timing for computing the interpolation for every one output of data values.

Variant Example 1 (FIGS. 22–24):

The computation of the interpolation as described hereinabove is directed to the case where one cycle portion is computed in a comprehensive manner. In this case, the amount of computations to be made at one time becomes very large. In order to reduce the burden to be imposed upon the control system by reducing the amount of the computations at one time, it is preferred to execute the computation of the interpolation for gaining a one data value at every timing of one output of the data value. Specifically, as shown in FIG. 24, the timing of the output of the previous data, with the basic sampling cycle of $\Delta t$, is shown at its upper side, and the timing of the computation of the interpolation of the current data is shown at its lower side. In other words, although the data value is generated at every sampling cycle $\Delta t$, the computation of the interpolation is executed immediately after the end of the output of the previous data value and is finished at the time when all the previous data values have been generated. The arrangement of this system can execute the computation of the interpolation during an vacant period of time extending from the output of a certain data value to the output of the following data value.

Figure 22:
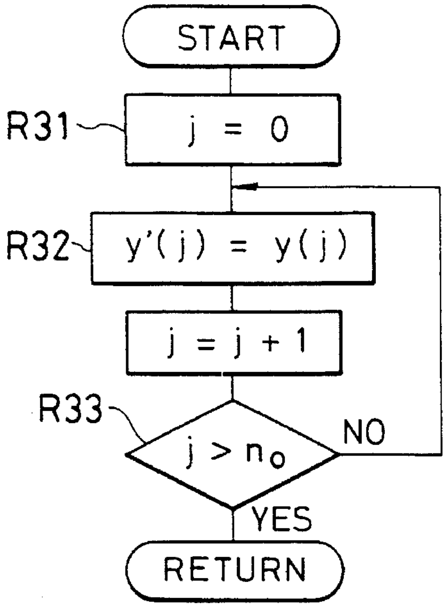
FIG. 22 is a flowchart for computing the interpolation for every one output of data values.
Figure 23:
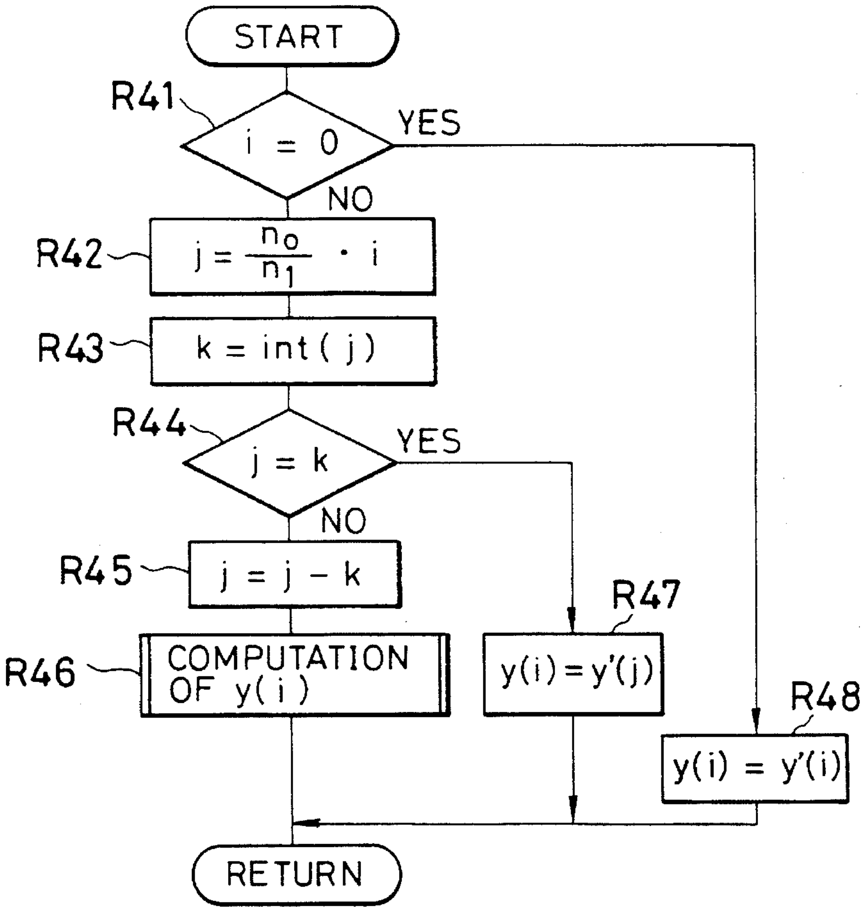
FIG. 23 is a flowchart for computing the interpolation for every one output of data values.

The control as described hereinabove can be specifically carried out in the manner as shown in FIGS. 22 and 23. FIG. 22 is directed to the processing to be executed at the time when all the previous data values have been generated and to the processing for changing the temporary data as shown in FIG. 17(2) into the final current data as shown in FIG. 17(3). FIG. 23 is directed to the processing for the computation of the interpolation to be executed immediately after one of the previous data values has been generated. The control contents as shown in FIG. 23 differ from those as shown in FIGS. 18 and 19 in that one value is obtained by the computation of the interpolation.

Figure 25:
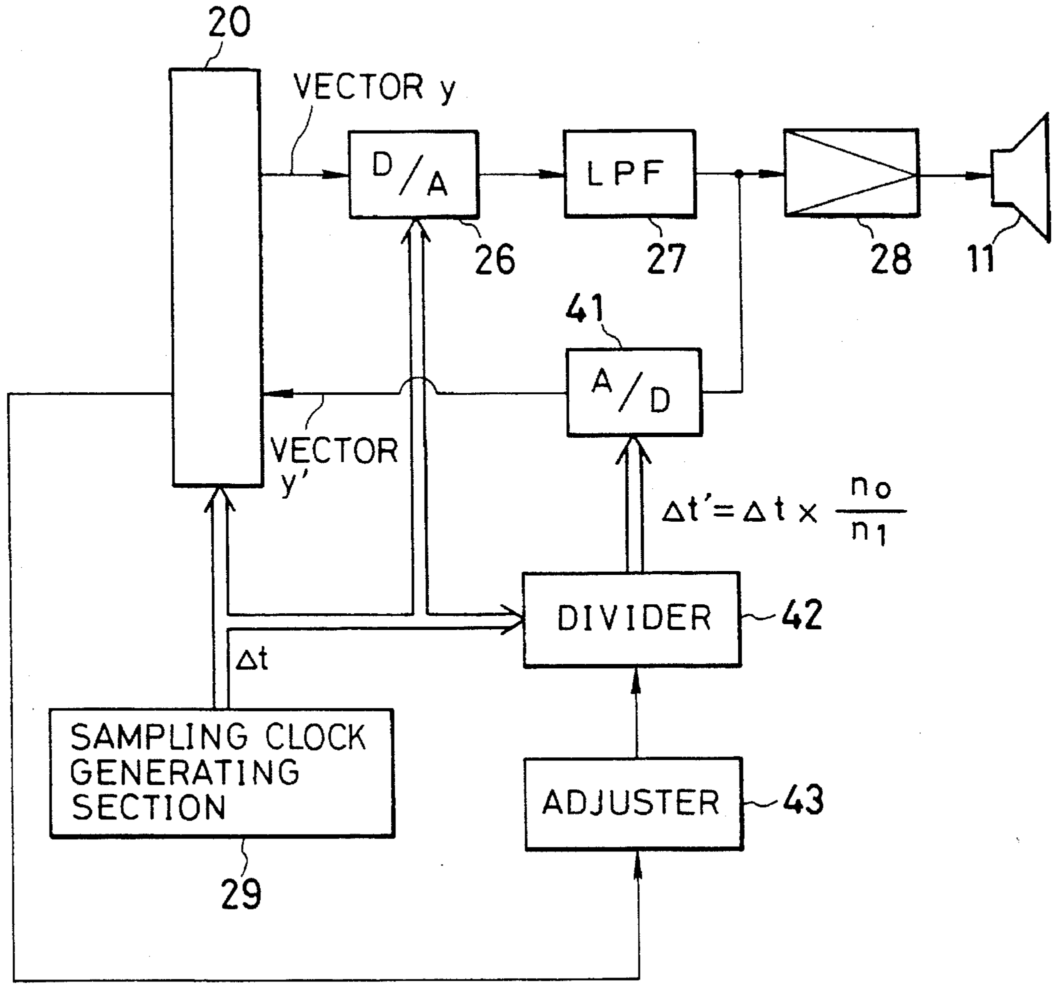
FIG. 25 is a schematic representation showing an example of a circuit for use in contracting or extending the whole wave form of vibrations by executing analog processing.

Variant Example 2 (FIG. 25):

FIG. 25 shows the instance where the whole vibration wave form is extended or contracted by analog processing. As the previous data passes through the D/A converter 26 and the low-pass filter 27 for the speaker 11, the signals passed through the low-pass filter 27 are arranged to be returned again to the control section 20 through the A/D converter 41. Then, the sampling cycle of the A/D converter 41 is set by a divider circuit 42, and the sampling cycle of the divider circuit 42 is set by a sampling adjuster 43 in response to instruction signals from the control section 20 so as to a value corresponding to a ratio of the data number of the previous data to the data number of the current data.

In this example, the extension or contraction of the whole vibration wave form can be executed by general techniques, such as D/A conversion or A/D conversion, and conventional D/A converters for the speaker 11 can be utilized for this purpose. Hence, the structure of the system can be simplified and the costs of the system can be reduced greatly, compared with the system which requires a D/A converter exclusively for the extension or contraction of the vibration wave form.

Figure 26:
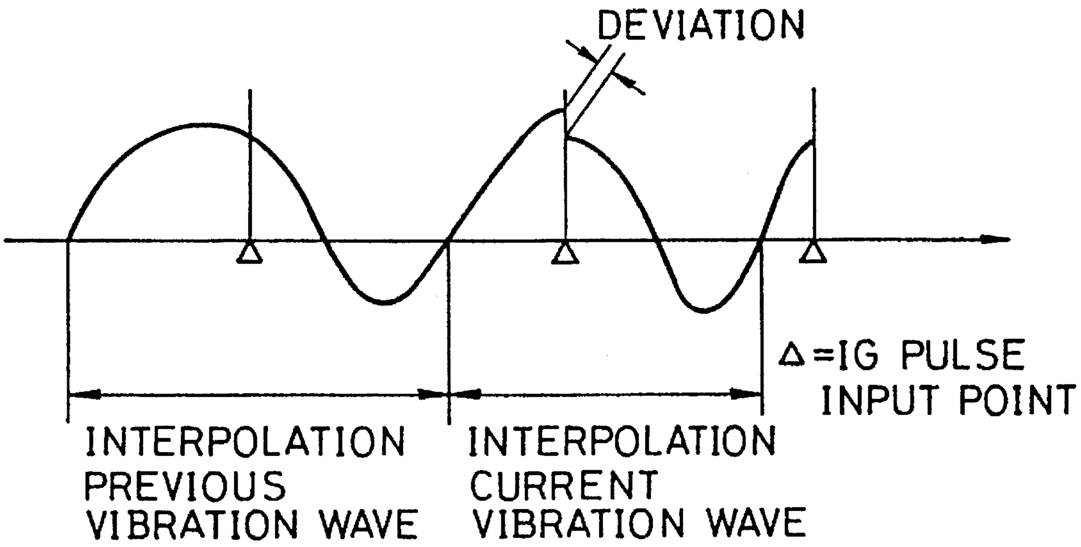
FIG. 26 is a diagram showing a deviation in the position of continuation between the wave form of the previous vibrations and the wave form of the current vibrations.
Figure 27:
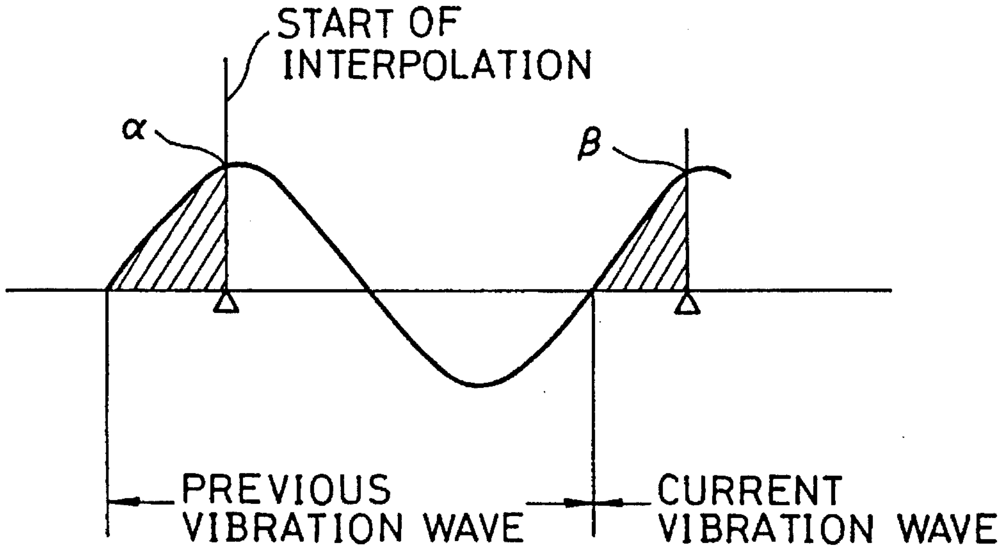
FIG. 27 is a diagram showing the preferable timing of starting the interpolation or analog processing for preventing or reducing the deviation as shown in FIG. 26.

Variant Example 3 (FIGS. 26–27):

FIGS. 26–27 show a preferred example of setting the timing of starting the interpolation or the analog processing. When the vibration wave form is extended or contracted as a whole by the interpolation or the analog processing, there is the possibility that such a deviation between the terminal value of the previous vibration wave form and the first value of the current vibration wave form becomes bigger, as shown in FIG. 26. If the data value always becomes zero at the time when the IG pulse has been entered as a reference for determining the changes of cycles, no problem with deviation occurs; however, as a matter of fact, the data value is not always zero at the time when the IG pulse has been entered.

Such a deviation can be reduced or avoided by starting the interpolation or the analog processing from the phase at the time of entry of the IG pulse, as shown in FIG. 27. In FIG. 27, the hatched areas resemble in shape and the phase components at the time of entry of the IG pulse, i.e. data values $\alpha$ and $\beta$, are substantially equal to each other.

Figure 28:
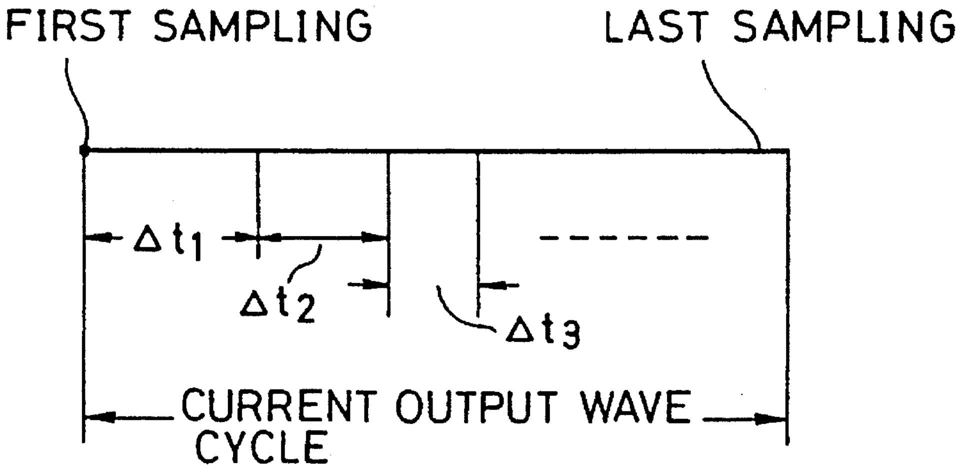
FIG. 28 is a diagram showing a preferred example of setting a sampling cycle for the interpolation or analog processing for preventing or reducing the deviation as shown in FIG. 26.

Variant Example 4 (FIG. 28):

FIG. 28 shows the techniques for appropriately setting the timing of starting the interpolation or the analog processing in order to prevent or reduce a deviation, from the point of view similar to the Variant Example 3. In this example, the sampling cycle for the interpolation or the analog processing is made smaller continually and gradually when the vibration wave form is extended. On the other hand, the sampling cycle therefor is made larger continually and gradually when the vibration wave form is contracted. In these cases, the deviation can be made possible smallest (changes of the weight for focusing the reproducibility of the previous vibration wave form on which phase portion).

As shown in FIG. 28, the sampling cycles for the interpolation or the analog processing are arranged so as to be reduced by τ portion in arithmetical progression. It can also be noted that the sampling cycles therefor can also be reduced in geometrical progression.

The control system according to this invention has been described above by way of examples and is not restricted thereto. Further, the control system can encompass the following embodiments.

1. As a second vibration source, there may be utilized any conventional actuator such as an actuator (built in an engine mounting member) interposed, for example, between the engine and the vehicle body, in addition to the speakers.

2. As a first vibration source, there may be employed an appropriate device loaded in the vehicle, which can cause periodic noises, in addition to the engine.

3. When the engine functions as the first vibration source, the first periodic vibration source to be reduced can be chosen from secondary vibrations, quarterly vibrations, sixth vibrations, and the like.

What is claimed is:

1. A vibration control system for an automotive vehicle so adapted as to reduce periodic vibrations generated by a first vibration source in a predetermined space of the vehicle, comprising:

a cycle detecting means for detecting a cycle of first vibrations;

a second vibration source for generating second vibrations for reducing a vibration energy of said first vibrations;

a vibration detecting means for detecting vibrations in the predetermined space thereof;

a vibration energy setting means for setting a vibration energy of the second vibrations generated from said second vibration source at every one cycle detected by said cycle detecting means and forming a data to be currently generated on the basis of the previous data corrected by a data length correcting means; and a correction means for correcting an output from said vibration energy setting means on the basis of an output from said vibration detecting means as well as a transmission characteristic between said vibration detecting means and said second vibration source;

wherein said data length correcting means for correcting a previous data causes the number of data contained in a data length of data of the previously generated second vibrations to agree with the number of data corresponding to a data length of data of the currently generating second vibrations, when the data length of the data of the currently generating second vibrations to be set in correspondence with a current cycle differs from the data length of the data of the previously generated second vibrations set in correspondence with a previous cycle of the previously generated second vibrations.

2. A vibration control system as claimed in claim 1, wherein said data length correcting means is arranged to correct a data length so as to provide a vibration wave form resembling a vibration wave form of the second vibrations generated previously.

3. A vibration control system for an automotive vehicle so adapted as to reduce periodic vibrations generated by a first vibration source in a predetermined space of the vehicle, comprising:

a cycle detecting means for detecting a cycle of first vibrations;

a second vibration source for generating second vibrations for reducing a vibration energy of said first vibrations;

a vibration detecting means for detecting vibrations in the predetermined space thereof;

a vibration energy setting means for setting a vibration energy of the second vibrations generated from said second vibration source at every one cycle detected by said cycle detecting means and forming a data to be currently generated on the basis of the previously generated data corrected by a data length correcting means; and a correction means for correcting on output from said vibration energy setting means on the basis of an output from said vibration detecting means as well as a transmission characteristic between said vibration detecting means and said second vibrations source;

wherein said data length correcting means inserts an estimated data value into a data length of a previous data or deletes a data value therefrom so as to cause the number of data contained in a data length of data of the previously generated second vibrations to agree with the number of data corresponding to a current data length, when the data length of the data of the currently generating second vibrations to be set in correspondence with a current cycle differs from the data length of the data of the previously generated second vibrations set in correspondence with a previous cycle of the previously generated second vibrations.

4. A vibration control system as claimed in claim 3, wherein plural estimated data values are inserted in positions spread in the data length of the previous data or plural data values are deleted from positions spread therein.

5. A vibration control system as claimed in claim 3, wherein said estimated data value is set as a data value identical to a data value which exists immediately ahead of or immediately behind the position in which said estimated data value is inserted and which is selected from the data values set in the data length of the previous data.

6. A vibration control system as claimed in claim 3, wherein said estimated data value is set as a mean value of two data values which exist immediately ahead of and immediately behind the position in which the estimated data value is inserted and which are selected from the data values set in the data length of the previous data.

7. A vibration control system as claimed in claim 3, wherein a data value to be replaced in the position from which the previous data value has been deleted is set as an arithmetic mean value between the previous data value and a data value immediately ahead of or immediately behind the previous data value.

8. A vibration control system as claimed in claim 3, wherein the position in which the estimated data value is inserted or the position from which the data value is deleted is arranged so as to vary at every cycle.

9. A vibration control system for an automotive vehicle so adapted as to reduce periodic vibrations generated by a first vibration source in a predetermined space of the vehicle, comprising:

a cycle detecting means for detecting a cycle of first vibrations;

a second vibration source for generating second vibrations for reducing a vibration energy of said first vibrations;

a vibration detecting means for detecting vibrations in the predetermined space thereof;

a vibration energy setting means for setting a vibration energy of the second vibrations generated from said second vibration source energy at every one cycle detected by said cycle detecting means and forming a data to be currently generated on the basis of the previously generated data corrected by a data length correcting means; and a correction means for correcting an output from said vibration energy setting means on the basis of an output from said vibration detecting means as well as a transmission characteristic between said vibration detecting means and said second vibration source;

wherein said data length correcting means extends or contracts an entire wave shape of the previously generated second vibrations so as to cause the number of data contained in the data length of the previously generated second vibrations to agree with the number of data corresponding to a current data length, when the data length of the data of the currently generated second vibrations to be set in correspondence with a current cycle differs from the data length of the data of the previously generated second vibrations set in accordance with a previous cycle of the previously generated second vibrations.

10. A vibration control system as claimed in claim 9, wherein said data length correcting means is arranged to provide a data value of the currently generating second vibrations by subjecting each of the data values of the previously generated second vibrations to interpolation.

11. A vibration control system as claimed in claim 10, wherein said interpolation is executed whenever one data value in the second vibrations is generated.

12. A vibration control system as claimed in claim 9, wherein said data length correcting means is arranged to provide current second vibrations by subjecting the previously generated second vibrations to analog processing.

13. A vibration control system as claimed in claim 12, wherein:

a digital signal corresponding to the second vibrations is set so as to be generated from said first vibration source through a A/D converter; and said analog processing by said data length correcting means is executed by the D/A converter for the second vibration source.

14. A vibration control system as claimed in claim 9, wherein:

said first vibration source is an internal combustion engine of a spark ignition type in which the engine is ignited with a spark plug;

said cycle detecting means for detecting a rotational cycle of the engine on the basis of an ignition pulse of the engine; and said data length correcting means is arranged to start extension or contraction of a wave form for correcting the data length from a phase component, as a starting point, corresponding to the time when the ignition pulse is entered.

15. A vibration control system as claimed in claim 9, wherein the sampling cycle for extending or contracting the wave form by said data length correcting means is arranged so as to vary continually and gradually.

16. A vibration control system as claimed in any one claim of claims 1 to 15, wherein:

said first vibration source is an internal combustion engine for driving a vehicle; and said predetermined space is a vehicle compartment.

17. A vibration control system as claimed in claim 16, wherein said second vibration source is a speaker for generating the second vibrations into the vehicle compartment.

* * * * *